US009868983B2

(12) United States Patent
Chae et al.

(10) Patent No.: US 9,868,983 B2
(45) Date of Patent: Jan. 16, 2018

(54) METHOD FOR DETECTING NUCLEIC ACIDS BY PROMOTING BRANCHED DNA COMPLEX FORMATION

(75) Inventors: Chi-Bom Chae, Seoul (KR); Kyung-Tae Kim, Seoul (KR); Jong Hun Kang, Seoul (KR)

(73) Assignee: Sugentech, Inc., Daejeon (KR)

(*) Notice: Subject to any disclaimer, the term of this patent is extended or adjusted under 35 U.S.C. 154(b) by 210 days.

(21) Appl. No.: 13/603,190

(22) Filed: Sep. 4, 2012

(65) Prior Publication Data
US 2013/0078629 A1    Mar. 28, 2013

Related U.S. Application Data
(63) Continuation of application No. PCT/KR2011/001452, filed on Mar. 3, 2011.

(30) Foreign Application Priority Data
Mar. 4, 2010 (KR) .................. 10-2010-0019539

(51) Int. Cl.
C12Q 1/68 (2006.01)
(52) U.S. Cl.
CPC .................. C12Q 1/686 (2013.01)
(58) Field of Classification Search
USPC .............................. 435/6.11, 6.12
See application file for complete search history.

(56) References Cited

U.S. PATENT DOCUMENTS

| 6,465,183 B2 | 10/2002 | Wolber | |
| 2005/0266466 A1 | 12/2005 | Ermantraut et al. | |
| 2008/0008990 A1* | 1/2008 | Chae et al. | 435/5 |
| 2008/0193934 A1 | 8/2008 | Woolwine | |
| 2008/0305966 A1 | 12/2008 | Tung | |
| 2009/0143243 A1* | 6/2009 | Gunning et al. | 506/9 |

FOREIGN PATENT DOCUMENTS

| EP | 0892070 A2 | 1/1999 |
| WO | 9402634 A1 | 2/1994 |
| WO | 9707235 A2 | 2/1997 |
| WO | 2007/079129 | 7/2007 |
| WO | 2009/105739 | 8/2009 |

OTHER PUBLICATIONS

Volokhov D, Rasooly A, Chumakov K, Chizhikov V. Identification of *Listeria* species by microarray-based assay. J Clin Microbiol. Dec. 2002; 40(12):4720-8.*
Lee TM, Hsing IM. Sequence-specific electrochemical detection of asymmetric PCR amplicons of traditional Chinese medicinal plant DNA. Anal Chem. Oct. 1, 2002; 74(19):5057-62.*
Oh SJ, Ju J, Kim BC, Ko E, Hong BJ, Park JG, Park JW, Choi KY. DNA microarrays on a dendron-modified surface improve significantly the detection of single nucleotide variations in the p53 gene. Nucleic Acids Res. Jun. 6, 2005; 33(10):e90.*
Tao Q, Wang X, Bao H, Wu J, Shi L, Li Y, Qiao C, Yakovlevich SA, Mikhaylovna PN, Chen H. Detection and differentiation of four poultry diseases using asymmetric reverse transcription polymerase chain reaction in combination with oligonucleotide microarrays. J Vet Diagn Invest. Sep. 2009; 21(5):623-32.*
Laassri M, Chizhikov V, Mikheev M, Shchelkunov S, Chumakov K. Detection and discrimination of orthopoxviruses using microarrays of immobilized oligonucleotides. J Virol Methods. Sep. 2003; 112(1-2):67-78.*
Lee et al. (2003b). Microfabricated PCR-electrochemical device for simultaneous DNA amplification and detection. Lab Chip. May 2003; 3(2):100-5. Epub Apr. 17, 2003.*
Kerman K, Vestergaard M, Nagatani N, Takamura Y, Tamiya E. Electrochemical genosensor based on peptide nucleic acid-mediated PCR and asymmetric PCR techniques: Electrostatic interactions with a metal cation. Anal Chem. Apr. 1, 2006; 78(7):2182-9.*
Wang et al., 1998, Dendritic Nucleic Acid Probes for DNA Biosensors. J. Am. Chem. Soc. 120, 8281-8282.*
Lay MJ, Wittwer CT. Real-time fluorescence genotyping of factor V Leiden during rapid-cycle PCR. Clin Chem. Dec. 1997; 43(12):2262-7.*
Pound E, Ashton JR, Becerril HA, Woolley AT. Polymerase chain reaction based scaffold preparation for the production of thin, branched DNA origami nanostructures of arbitrary sizes. Nano Lett. Dec. 2009; 9(12):4302-5.*
Tsai SP, Wong A, Mai E, Chan P, Mausisa G, Vasser M, Jhurani P, Jakobsen MH, Wong WL, Stephan JP. Nucleic acid capture assay, a new method for direct quantitation of nucleic acids. Nucleic Acids Res. Mar. 15, 2003; 31(6):e25.*
Tsongalis GJ. Branched DNA technology in molecular diagnostics. Am J Clin Pathol. Sep. 2006; 126(3):448-53.*
Flagella M, Bui S, Zheng Z, Nguyen CT, Zhang A, Pastor L, Ma Y, Yang W, Crawford KL, McMaster GK, Witney F, Luo Y. A multiplex branched DNA assay for parallel quantitative gene expression profiling. Anal Biochem. May 1, 2006; 352(1):50-60. Epub Mar. 2, 2006.*
Collins ML, Irvine B, Tyner D, Fine E, Zayati C, Chang C, Horn T, Ahle D, Detmer J, Shen LP, Kolberg J, Bushnell S, Urdea MS, Ho DD. A branched DNA signal amplification assay for quantification of nucleic acid targets below 100 molecules/ml. Nucleic Acids Res. Aug. 1, 1997;25(15):2979-84.*
Guo Z, Guilfoyle RA, Thiel AJ, Wang R, Smith LM. Direct fluorescence analysis of genetic polymorphisms by hybridization with oligonucleotide arrays on glass supports. Nucleic Acids Res. Dec. 11, 1994; 22(24):5456-65.*
Kim KT, Na CH, Yun YM, Hwang TS, Kim SN, Chae CB. Dramatic increase in signal by integration of polymerase chain reaction and hybridization on surface of DNA microarray. Anal Biochem. Jan. 1, 2010; 396(1):139-45. Epub Aug. 29, 2009.*
Stears RL, Getts RC, Gullans SR. A novel, sensitive detection system for high-density microarrays using dendrimer technology. Physiol Genomics. Aug. 9, 2000;3(2):93-9.*
Poddar SK. Symmetric vs asymmetric PCR and molecular beacon probe in the detection of a target gene of adenovirus. Mol Cell Probes. Feb. 2000; 14(1):25-32.*

(Continued)

*Primary Examiner* — Angela M Bertagna
*Assistant Examiner* — Olayinka Oyeyemi
(74) *Attorney, Agent, or Firm* — Greer, Burns & Crain, Ltd.

(57) ABSTRACT

Disclosed is a method for detecting nucleic acids by promoting branched DNA complex formation. The target nucleic acid detection signal and sensitivity can be dramatically increased by promoting self assembly of branched DNA between a plurality of amplified DNA targets and a single-chain oligonucleotide probe, by means of the integrated implementation of PCR, thermal denaturation and hybridization in a single reaction mixture.

16 Claims, 13 Drawing Sheets

(56) References Cited

OTHER PUBLICATIONS

European Patent Office, Supplementary European Search Report for Application No. EP 11 75 0911, dated Sep. 24, 2013.
Pierce, Kenneth E. et al., Detection of Cystic Fibrosis Alleles from Single Cells Using Molecular Beacons and a Novel Method of Asymmetric Real-Time PCR, Molecular Human Reproduction, Oxford University Press, GB-BE, vol. 9, No. 12, Dec. 1, 2013, pp. 815-820.
Thomas M.H. Lee et al., Sequence-Specific Electrochemical Detection of Asymmetric PCR Amplicons of Traditional Chinese Medicinal Plant DNA, Analytical Chemistry, vol. 74, No. 19, Oct. 1, 2002, pp. 5057-5062.
Kyung-Tae Kim et al., Dramatic Increase in the Signal and Sensitivity of Detection via Self-Assembly of Branched DNA, Molecules and Cells, vol. 32, No. 4, Aug. 23, 2011, pp. 367-374.
Wong, D. M. et al. "Branch capture reactions: displacers derived from asymmetric PCR." Nucleic Acids Research. May 11, 1999, vol. 19, No. 9, pp. 2251-2259.
Shchepinov, M. S. et al. "Oligonucleotide dendrimers: synthesis and use as polylabelled DNA probes." Nucleic Acids Research, Nov. 15, 1997, vol. 25, No. 22, pp. 4447-4454.
International Search Report of PCT/KR2011/001452 dated Nov. 18, 2011.

\* cited by examiner

① On-slide RT-PCR (asymmetric 5p:50p) and hybridization
② RT-PCR (asymmetric 5p:50p) product in 3xSSC
③ RT-PCR (symmetric 5p:5p) product in 3xSSC

• Probe sequence is partial complementary with BCR B3 sequence

SEQUENCE LISTING

```
<160> NUMBER OF SEQ ID NOS: 9

<210> SEQ ID NO 1
<211> LENGTH: 29
<212> TYPE: DNA
<213> ORGANISM: Artificial Sequence
<220> FEATURE:
<223> OTHER INFORMATION: forward primer

<400> SEQUENCE: 1
gatggtagta tggttcatac tggctttgg                                            29

<210> SEQ ID NO 2
<211> LENGTH: 29
<212> TYPE: DNA
<213> ORGANISM: Artificial Sequence
<220> FEATURE:
<223> OTHER INFORMATION: reverse primer

<400> SEQUENCE: 2
gcatcagagg taaccataga accactagg                                            29

<210> SEQ ID NO 3
<211> LENGTH: 29
<212> TYPE: DNA
<213> ORGANISM: Artificial Sequence
<220> FEATURE:
<223> OTHER INFORMATION: forward primer

<400> SEQUENCE: 3
gatggtgata tggtagatac aggatttgg                                            29

<210> SEQ ID NO 4
<211> LENGTH: 29
<212> TYPE: DNA
<213> ORGANISM: Artificial Sequence
<220> FEATURE:
<223> OTHER INFORMATION: reverse primer

<400> SEQUENCE: 4
gcgtcagagg ttaccataga gccactagg                                            29

<210> SEQ ID NO 5
<211> LENGTH: 29
<212> TYPE: DNA
<213> ORGANISM: Artificial Sequence
```

```
<220> FEATURE:
<223> OTHER INFORMATION: HPV16 capture probe

<400> SEQUENCE: 5
ctctgggtct actgcaaatt tagccagtt                                              29

<210> SEQ ID NO 6
<211> LENGTH: 23
<212> TYPE: DNA
<213> ORGANISM: Artificial Sequence
<220> FEATURE:
<223> OTHER INFORMATION: HPV18 capture probe

<400> SEQUENCE: 6
cacaggtatg cctgcttcac ctg                                                    23

<210> SEQ ID NO 7
<211> LENGTH: 19
<212> TYPE: DNA
<213> ORGANISM: Artificial Sequence
<220> FEATURE:
<223> OTHER INFORMATION: forward primer

<400> SEQUENCE: 7
gggagcagca gaagaagtg                                                         19

<210> SEQ ID NO 8
<211> LENGTH: 25
<212> TYPE: DNA
<213> ORGANISM: Artificial Sequence
<220> FEATURE:
<223> OTHER INFORMATION: reverse primer

<400> SEQUENCE: 8
cctaagaccc ggagcttttc acctt                                                  25

<210> SEQ ID NO 9
<211> LENGTH: 23
<212> TYPE: DNA
<213> ORGANISM: Artificial Sequence
<220> FEATURE:
<223> OTHER INFORMATION: ABL A2 capture probe

<400> SEQUENCE: 9
gtgaagccgc tcgttggaac tcc                                                    23
```

METHOD FOR DETECTING NUCLEIC ACIDS BY PROMOTING BRANCHED DNA COMPLEX FORMATION

CROSS-REFERENCE TO RELATED APPLICATIONS

This application claims priority of PCT Application No. PCT/KR2011/001452, filed on Mar. 3, 2011 and Korean Application No. 10-2010-0019539, filed on Mar. 4, 2010, the entire disclosures of which are incorporated herein by reference.

TECHNICAL FIELD

The present disclosure relates to a method for detecting nucleic acids of which a detection signal and sensitivity are dramatically increased by promoting branched DNA formation. To be more specific, the present disclosure relates to a method for dramatically increasing a target nucleic acid detection signal and sensitivity by promoting self-assembly of a branched DNA between a short nucleic acid probe and multiple amplified target DNAs by means of integrated implementation of a PCR (Polymerase Chain Reaction) and hybridization in a single reaction mixture within a solution or on a solid support surface.

BACKGROUND ART

Typically, a diagnostic method using a short nucleic acid probe (generally, DNA or PNA) having a single chain has been used for many purposes, such as for checking or detecting disease causing-genes, mutations, infectious agents (for example, viruses, microorganisms, and the like), genotyping, gene expression, and the like. Generally, the short nucleic acid probe has been used while being fixed on various solid surfaces including a glass plate surface, a metal plate surface, and a bead surface. By way of example, one of advantages of a DNA micro array (or a DNA chip) using a short nucleic acid probe is that many different target nucleic acid sequences can be analyzed at the same time. Such a technique has been used in hospitals and clinics for diagnosis, and other various techniques have been combined and optimized for easy use and/or reliable determination for clinical diagnoses.

Typically, the diagnostic method using a short nucleic acid probe requires a long process as follows: (a) extracting a nucleic acid (DNA or RNA) from a biological sample (for example, tissue, a cell, blood, serum, a body fluid, and the like); (b) amplifying a target nucleic acid; and (c) finally, hybridizing the amplified nucleic acid sequence with a short nucleic acid probe fixed on a solid (for example, glass slide or bead) surface. Herein, in order to detect a RNA sequence, a RNA needs to be converted into a DNA by means of a reverse transcription reaction prior to the amplification.

As can be seen from the typical process required for detecting a target nucleic acid, a molecular biological diagnostic method using a short nucleic acid probe requires a lot of time and effort and it is inconvenient. Therefore, a simple process is required for conveniently and economically analyzing a nucleic acid sequence with high throughput, and it is important, particularly, for clinical diagnoses in hospitals and clinics.

Further, sensitivity of a method used for detecting a hybridized product is important. Detection sensitivity is important, particularly, in detecting infectious agents (for example, viruses, microorganisms, and the like) and also important for prognosis of treatment. By way of example, the success or failure of treatment for infectious agents can be determined by the number of residual infectious agents remaining in human body fluids (for example, blood). As another example, the success or failure of cancer treatment can be determined by existence of a cancer causing gene (i.e. existence of a cancer cell).

Typically, it has been known that detection sensitivity of a target nucleic acid sequence using a short nucleic acid probe fixed on a solid surface is lower several times than sensitivity of a real-time PCR. Therefore, a method for improving detection sensitivity using a short nucleic acid probe and desirably, a detection method with improved sensitivity capable of detecting a single target molecule need to be developed.

There has been used a diagnostic method in which a branched DNA connected with multiple labels is synthesized without amplifying a diagnosis target nucleic acid and a high signal and sensitivity thereof can be obtained through a bipartite oligonucleotide probe, i.e. an oligonucleotide that connects the branched DNA with the diagnosis target nucleic acid combined with a capture probe on a solid surface by means of hybridization. However, according to this method, the branched DNA needs to be synthesized outside and the bipartite oligonucleotide probe that recognizes a diagnosis target as well as the capture probe fixed on the solid surface needs to be synthesized. Although this method has high sensitivity, it requires a lot of time and it is inconvenient to perform many processes.

DISCLOSURE OF THE INVENTION

Problems to Be Solved by the Invention

In view of the foregoing, the present disclosure provides a method for detecting a target nucleic acid by using a short nucleic acid probe and specifically, provides a method for dramatically increasing a detection signal and sensitivity by promoting self-assembly of a branched DNA complex between a short nucleic acid probe and multiple amplified target DNAs.

Means for Solving the Problems

In accordance with an aspect of the present disclosure, there is provided a method for detecting a target nucleic acid molecule from a sample, the method comprising: integrated implementing of amplification, thermal denaturation, and hybridization of a target nucleic acid molecule to be detected in a single reaction mixture under presence of a nucleic acid probe including a sequence entirely or partially complementary to the target nucleic acid molecule to be detected to promote formation of a branched nucleic acid complex by hybridizing multiple amplified nucleic acid molecules with the nucleic acid probe; and detecting the hybridized branched nucleic acid complex.

In accordance with an illustrative embodiment, the amplification is implemented by means of an asymmetric polymerase chain reaction (asymmetric PCR). Even if a typical PCR is implemented, when primer of an excessive concentration is used, the branched nucleic acid complex formation can be promoted.

In accordance with an illustrative embodiment, the integrated implementing of amplification, thermal denaturation, and hybridization includes self-assembly of the branched nucleic acid complex.

In accordance with an illustrative embodiment, the integrated implementing of amplification, thermal denaturation, and hybridization is implemented by adjusting a temperature, a temperature cycle time, and a temperature cycle number using a thermocycler.

The integration of the amplification and hybridization of the target nucleic acid molecule means that amplification and hybridization are implemented in an integrated manner in a single reaction mixture on a solid support surface (for example, a surface of a microarray, a surface in a container or a tube, or a bead surface) or within a solution in a container. If a thermo-cycler is combined with the solid support or the container, integrated implementation of the amplification and hybridization can be easily achieved by adjusting a temperature of the solid support or the container, a temperature cycle time, and a temperature cycle number. Such adjustment can be programmed, so that a detection process can be automated. More details of integration of amplification and hybridization are described in International Patent Application No. PCT/US2006/049395 filed by the present inventors, the entire disclosures of which are incorporated herein by reference.

In accordance with an illustrative embodiment, the sample includes whole blood, serum, a body fluid, a body tissue, a cell, a microorganism, a virus, or a virus particle. Any sample can be used if it contains a target nucleic acid to be detected.

In accordance with an illustrative embodiment, wherein the sample includes a nucleic acid molecule which is not separated and purified. A sample in which a nucleic acid molecule is separated and purified can be used.

In accordance with an illustrative embodiment, if the sample is a sample in which a nucleic acid molecule is not separated and purified, before the amplification and hybridization are implemented in an integrated manner, a surfactant treatment, an enzyme treatment or a heating treatment may be additionally performed in order to expose a nucleic acid of the sample, but it is not limited thereto. More details of integrated implementation of amplification and hybridization without separating and purifying a nucleic acid molecule are described in International Patent Application No. PCT/US2009/034809 filed by the present inventors, the entire disclosures of which are incorporated herein by reference.

In accordance with an illustrative embodiment, the target nucleic acid molecule to be detected is selected from a group consisting of a nucleic acid molecule existing in a cell-free sample; a nucleic acid molecule existing in a virus particle or a non-eukaryotic cell; and a nucleic acid molecule of a pathogen.

In accordance with an illustrative embodiment, the target nucleic acid molecule to be detected includes a mutated sequence, and the probe is complementary to the target nucleic acid molecule including the mutated sequence.

In accordance with an illustrative embodiment, the target nucleic acid molecule includes a DNA or a cDNA which is reverse-transcribed from an RNA molecule.

In accordance with an illustrative embodiment, the target nucleic acid molecule includes a RNA molecule, and the integrated implementing of amplification, thermal denaturation, and hybridization includes integrated implementation of reverse transcription, amplification, thermal denaturation, and hybridization of the target RNA molecule in the single reaction mixture. The amplification is implemented by means of an asymmetric PCR. Even if a typical PCR is implemented, when primer of an excessive concentration is used, the branched nucleic acid complex formation can be promoted.

In accordance with an illustrative embodiment, the nucleic acid probe includes a single-stranded DNA or PNA sequence.

In accordance with an illustrative embodiment, the nucleic acid probe may exist, but is not limited to, within a solution or on a solid support. If the nucleic acid probe exists within a solution, amplification and hybridization of a target nucleic acid molecule can be implemented in an integrated manner within a single container. If the nucleic acid probe exists on a solid support, amplification and hybridization of a target nucleic acid molecule can be implemented in an integrated manner on the solid support.

The solid support may include various solid surfaces, for example, a plastic tube surface, a plastic well surface, a glass well surface, a bead surface, a glass slide surface, a metal surface and the like. Further, the solid support may be a microarray having multiple nucleic acid probes fixed thereto.

In accordance with an illustrative embodiment, + claim 15. Herein, as the linker molecule, various materials capable of connecting a nucleic acid probe to a solid support can be used. By way of example, a surface of a solid support such as a glass slide may be coated with various chemical materials to allow the nucleic acid probe to be fixed to the surface. The chemical materials need to fix the probe (DNA or PNA) to the solid support surface and minimize non-specific bonding and noise and may include, for example, amine and epoxy for fixing a DNA or silane, silyl or poly-L-lysine as a source of an aldehyde group. Neurodendrites (dendron or dendrimers) to be used in a biochip have been developed. If the neurodendrite is used as the linker molecule, a space with respect to a capture probe can be adjusted and steric hindrance can be reduced and also sensitivity can be increased. This result can be achieved by other methods. By way of example, if a biotin-nucleic acid probe is fixed to a glass slide surface coated withstreptavidin, this result can be achieved.

In accordance with an illustrative embodiment, the amplified target molecule can be detected by various methods publicly known in the art.

By way of example, if a reaction mixture used for an amplification reaction contains a fluorescence-labeled dNTP, it is possible to label an amplified nucleic material and also possible to use a radioactive isotope as a label. Further, an electrochemical detection and a double-chain nucleic acid bonding agent, for example, SYBR green usefully used after washing or cleaning a bonded material from a chip surface or a slide surface may be used. Furthermore, a biotin-labeled PCR primer is used during amplification of a target nucleic acid, so that detection may be performed by using streptavidin bonded with a chromophoric enzyme. Other detection means publicly known in the art may be used, and a labeled compound containing a radioactive or chemiluminescent residue instead of a fluorescent residue, or other means based on a chemical, enzymatic, physiochemical process or an antigen-antibody binding process may be used. By way of example, alkaline phosphatase, horseradish peroxidase, β-galactosidase, urease, luciferase, rhodamine, fluorescein, phycoerythrin, luminol, isoluminol, acridinium ester or fluorescent microsphere may be used as a detectable residue.

The amplified material on the solid support can be analyzed by a certain appropriate device publicly known in the art. By way of example, a commercial confocal laser scanner for obtaining images and a quantitative microarray analysis software for analyzing fluorescence intensity may be used to analyze DNAs after the hybridization.

In accordance with another aspect of the present disclosure, there is provided a method for detecting a target nucleic acid molecule from a sample, the method comprising: amplifying a target nucleic acid molecule to be detected by means of an asymmetric PCR; delivering a whole reaction mixture including the amplified target nucleic acid molecule to a solution or a solid support surface which includes a nucleic acid probe including a sequence entirely or partially complementary to the target nucleic acid molecule; performing hybridization within the solution or on the solid support to promote formation of a branched nucleic acid complex by hybridizing multiple amplified nucleic acid molecules with the nucleic acid probe; and detecting the hybridized branched nucleic acid complex, wherein thermal denaturation to the reaction mixture is implemented before or after the reaction mixture is delivered to the solution or the solid support surface.

Herein, the nucleic acid probe fixed on the solid support is used to easily analyze the branched nucleic acid complex formed with the nucleic acid probe. In accordance with an illustrative embodiment, it can be seen that an asymmetric PCR and a hybridization with a short nucleic acid probe.

In accordance with an illustrative embodiment, the asymmetric PCR may be implemented in a container separated from the solid support surface to deliver the whole reaction mixture to the solid support surface to which the nucleic acid probe is fixed, but the present disclosure is not limited thereto.

Even if a chain asymmetric PCR are implemented separately, the whole reaction mixture is delivered to the solid support surface to which the nucleic acid probe is fixed, so that formation of a branched nucleic acid complex can be promoted. Herein, all the process except the separated implementation of the asymmetric PCR may be performed in the same manner as described above with reference to the integrated implementation.

Effect of the Invention

In accordance with an example of the present disclosure, in detecting a target nucleic acid molecule in the field of molecular diagnosis as well as basic research, it is possible to detect a target DNA or RNA with detection sensitivity capable of detecting a single target nucleic acid molecule with a high signal (i.e. high reliability) by using a DNA chip technique. There is no precedent for detection of a single target DNA molecule with high reliability (high signal) by using a DNA microarray, and the sensitivity is equal to or much greater than a performance of the newest quantitative PCR.

In accordance with an example of the present disclosure, after a nucleic acid probe is fixed to a bead and an asymmetric PCR and hybridization are implemented, formation of a branched DNA can be measured by collecting the bead. After a nucleic acid probe is fixed to a surface of a plastic or glass container or a tube and the asymmetric PCR and hybridization are implemented, formation of a branched DNA can be measured. It can be seen from these examples that the present disclosure can be applied to various diagnostic methods. These examples can be used to automate a diagnosis.

A signal obtained from integrated implementation of an asymmetric PCR and hybridization in accordance with an example of the present disclosure is higher at least 25 times to 30 times than a typical protocol recommended by a commercial DNA chip diagnostic kit. Thus, high sensitivity of the integrated implementation process can be applied variously for detecting and identifying infectious agents such as viruses and microorganisms and for determining whether there are infectious agents in a body. Further, such an integrated implementation can be used for detecting cancer cells from many ordinary cells.

Self-assembly of a branched DNA complex through the integrated implementation of the present disclosure can be used to automate a gene diagnosis. That is, a device required for the PCR and a device required for the hybridization can be integrated and also, a required process, i.e. pipetting and transferring a sample, can be simplified.

There has been published a technique for increasing a signal and sensitivity by synthesizing a branched DNA bonded to a labeled molecule and connecting the branched DNA with a diagnosis target nucleic acid hybridized with a capture probe fixed to a solid through a bipartite oligonucleotide having a sequence site complementary to a diagnosis target nucleic acid and a sequence site complementary to the branched DNA. However, this technique is quite different from the formation of the branched DNA complex through the self-assembly. According to this technique, a diagnosis target gene is amplified through a PCR and a branched DNA complex is formed, so that a signal and sensitivity can be further increased. In addition, integrated implementation (PCR, thermal denaturation, and hybridization) is carried out in a single PCR mixture, so that a process can be simplified.

BRIEF DESCRIPTION OF THE DRAWINGS

FIG. 2(a) shows a primary bonded structure of a 29 nt capture probe and a reverse chain formed by a R primer. FIG. 2(b) shows that the bonded structure formed in FIG. 2(a) is bonded to two forward chains formed by two F primers, and, thus, a site to be bonded to two reverse chains is exposed. FIG. 2(c) shows that the bonded structure formed in FIG. 2(b) is bonded to two reverse chains, and, thus, a site to be bonded to two forward chains is exposed. Herein, • and ○ denote labeled molecules.

FIG. 3(a) shows a result of a symmetric PCR and an asymmetric PCR with a primer set A having a sequence entirely complementary to a HPV16 L1 site. FIG. 3(b) shows a result of an experiment with a genotyping primer set B. Lanes shown in FIGS. 3(a) and 3(b) are as follows: Lane 1—symmetric PCR+hybridization; Lane 2—symmetric PCR+capture probe+hybridization; Lane 3: asymmetric PCR+hybridization; and Lane 4: asymmetric PCR+capture probe+hybridization.

FIG. 4(a) is an image of EtBr staining. FIG. 4(b) is a Cy5 image. Asymmetric PCR+hybridization: Lane 1—Cy5-GP4F primer; Lane 2—Cy5-GP4R primer asymmetric PCR+capture probe+hybridization; Lane 3—Cy5-GP4F primer; and Lane 4—Cy5-GP4R primer. In case of DNAs of Lanes 3 and 4 treated with S1 nuclease: Lane 5—Cy5-GP4F primer; and Lane 6—Cy5-GP4R primer.

FIG. 5(a) is an image of EtBr staining. FIG. 5(b) is a Cy5 image. In case of integrated implementation without a capture probe: Lane 1—Cy5-GP4R; and Lane 2—Cy5-GP4F. In case of integrated implementation with a capture probe: Lane 3—Cy5-capture probe; Lane 4—Cy5-GP4R; and Lane 5—Cy5-GP4F.

FIG. 6(a) shows a state where an asymmetric PCR implemented with a capture probe is stopped (Lane 1), a state where hybridization is implemented without denaturation after an asymmetric PCR (Lane 2), and a state where denaturation is implemented at about 95° C. and hybridization is implemented at about 50° C. after an asymmetric PCR (Lane 3). FIG. 6(b) shows a state where an asymmetric PCR is implemented and denaturation and hybridization are implemented without a capture probe (Lane 1), a state where after an asymmetric PCR and thermal denaturation are implemented, a capture probe is added and hybridization is implemented (Lane 2), and a state where after an asymmetric PCR and thermal denaturation are implemented, a capture probe and EDTA are added and hybridization is implemented (Lane 3).

BEST MODE FOR CARRYING OUT THE INVENTION

Definition

Figure 1:
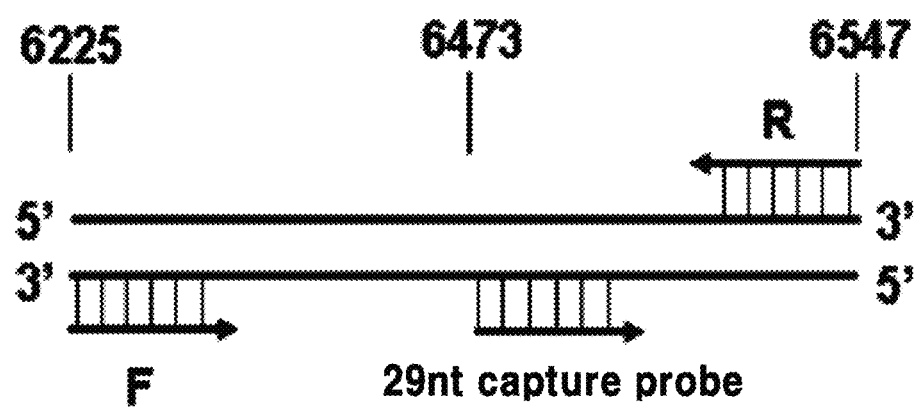
FIG. 1 schematically shows a L1 site of a HPV DNA used for genotyping the HPV DNA and shows a forward (F) PCR primer, a reverse (R) PCR primer, and a 29 nucleotide (nt) used as a HPV16 capture probe.

Although most terms used in the present disclosure can be understood by those skilled in the art, the following definitions are provided for better understanding. Even if any terms are not clearly defined, the terms should be understood as being accepted by those skilled in the art.

The term "asymmetric polymerase chain reaction (asymmetric PCR)" means a technique capable of generating an amplified single-chain DNA. In this reaction, one of two primers is used in excessive amount and a single-chain DNA can be amplified with the primer used in excessive amount.

The term "branched DNA" means an aggregated DNA in which three or more single-chain DNAs are partially hybridized with each other and have side chains.

The term "hybridization" means formation of a duplex between two chains of a single-chain DNA or formation of duplex between a DNA chain and a RNA chain by means of base complementarity.

The term "DNA denaturation" can be seen from a case where a single-chain DNA is needed to form in order for a complementary DNA chain to form a DNA having a double-stranded duplex by means of hybridization and a double-stranded DNA chain is separated at about 90° C. or more. The double-stranded DNA chain is separated at about pH 13 to about pH 14. At about 94° C. or about 95° C. described in the present disclosure, substantially the same result can be obtained. That is, the double-stranded DNA is divided into two single-stranded DNAs.

The term "solid support" means a substrate to which a capture probe for detecting a target nucleic acid may be fixed. Desirably, "solid support" may include a plane substrate such as a glass slide, a metal, and a plastic and may include a round substrate such as a glass bead, a plastic bead or a polymer bead and may also include substrates, such as a glass or plastic container, i.e. a tube, made of various materials.

The term "amplification" means that the number of copies of a specific nucleic acid is increased.

The term "detect" or its derivatives include a quantitative detection method and a qualitative detection method.

The term "comprise" or "include" means existence of features, numbers, steps, operations, components, parts or combinations thereof and does not exclude existence of one or more other features, numbers, steps, operations, components, parts or combinations thereof and possibility of adding them.

Hereinafter, a method for detecting a nucleic acid in accordance with the present disclosure will be explained in detail with reference to the accompanying drawings.

The present disclosure includes a method for promoting branched DNA formation between a fixed capture nucleic acid probe and an amplified target DNA by means of integrated implementation of asymmetric amplification, thermal denaturation, and hybridization of a DNA chain within a liquid or on a solid surface. In detecting a target nucleic acid molecule in the field of molecular diagnosis as well as basic research, it is possible to dramatically increase detection sensitivity capable of detecting a single target nucleic acid molecule with a high signal (i.e. high reliability) by using a DNA chip technique. This technique can also be used for detecting a RNA molecule with high sensitivity and signal by means of integrated implementation of reverse transcription, asymmetric amplification, and hybridization within a solution or on a solid support surface.

As depicted in FIG. 1, during a DNA diagnosis with a DNA chip, a small section of a DNA including a target DNA is amplified (and may be labeled during the amplification).

Figure 2:
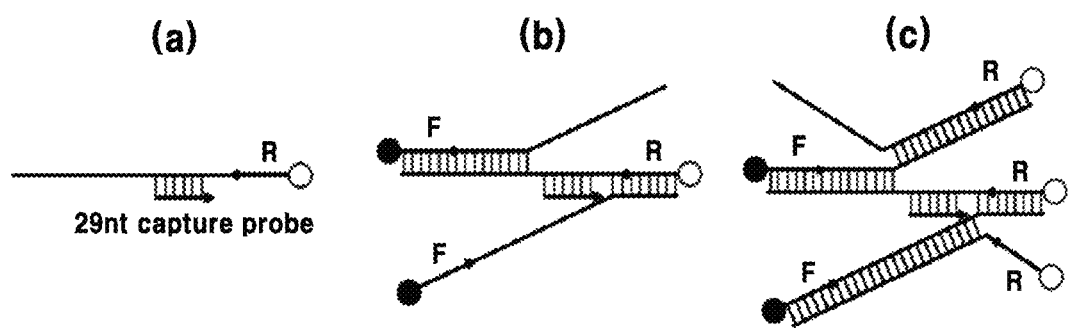
FIG. 2 shows a hybridization process.

FIG. 2 shows a hybridization process. FIG. 2(a) shows a primary bonded structure of a 29 nt capture probe and a reverse chain formed by a R primer during the hybridization process and shows that two sites where a forward chain can be bonded to the reverse chain are exposed. FIG. 2(b) shows that the bonded structure formed in FIG. 2(a) is bonded to two forward chains formed by two F primers, and, thus, a site to be bonded to two reverse chains is exposed. FIG. 2(c) shows that the bonded structure formed in FIG. 2(b) is bonded to two reverse chains, and, thus, a site to be bonded to two forward chains is exposed. If this process is repeatedly preformed, a huge complex, i.e. a branched DNA, where multiple PCR chains are bonded to a single oligonucleotide probe can be formed. If a labeled-PCR product is used, there may be a great increase in signal. Herein, • and ○ connected to the PCR primers denote labeled molecules. As depicted in FIG. 2, the amplified DNA is hybridized with a short capture nucleic acid probe corresponding to the small section of the amplified DNA. In theory, after a complementary chain of the amplified DNA (a chain extended by the reverse primer R in FIG. 1) bonds with a capture probe to form a duplex, a major section of the bonded and amplified DNA chain is opened to form a duplex together with another amplified chain (a chain extended by the forward primer F in FIG. 1) (FIG. 2(a)). After the forward chain is bonded to the reverse chain (FIG. 2(b)), two open sections of the forward chain can be bonded to two reverse chains, and, thus, a branched DNA (or an aggregated DNA) can be formed (see a model depicted in FIG. 2(c)). In theory, such a bonding process is repeated several times. If each PCR chain is labeled, a detection signal and sensitivity can be greatly increased.

Figure 3:
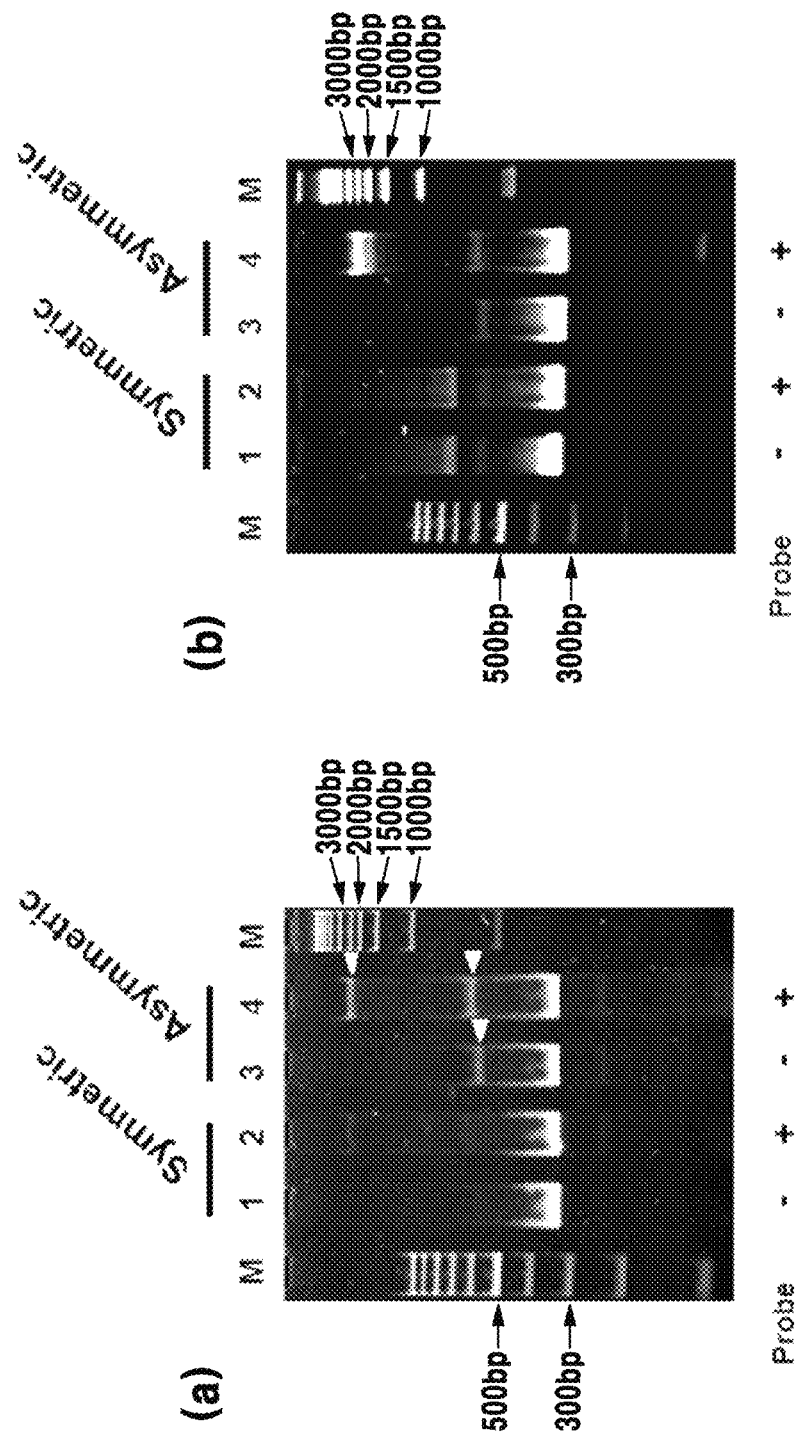
FIG. 3 is an electrophoresis result image proving assembly of aggutinates (or a branched DNA) between a capture probe and an asymmetric PCR product.
Figure 4:
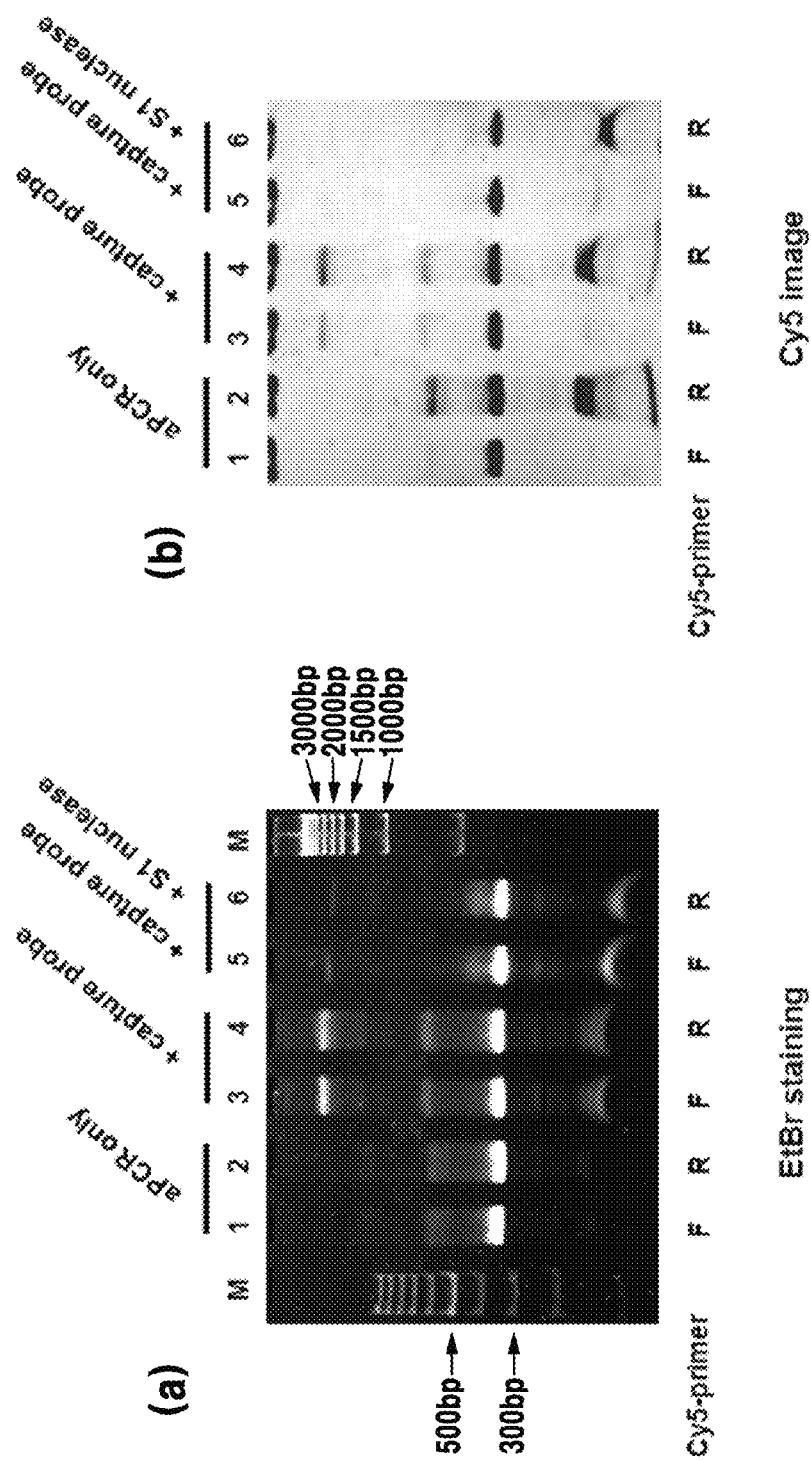
FIG. 4 is an electrophoresis result image showing that a branched DNA complex includes not a normal double-chain DNA but a single-chain site and a gap.

Formation of Huge Branched DNA Complex Between Capture Probe and Asymmetric PCR Product In order to prove assembly of a branched DNA between an amplified DNA and a capture probe, two kinds of primer sets are used. A primer set A is entirely complementary to a gene L1 of a HPV16 DNA and a primer set B includes several sequence changes in the primer set A so as to amplify a L1 site of about 40 kinds of HPV viruses (genotyping). The reason for this is to show that a branched DNA complex technique can be applied to diagnose whether or not there is HPV infection and diagnose a HPV type. These primer sets will be described in the following example 1. As depicted in FIG. 3(a), if an asymmetric PCR product using the primer set A is denatured at about 95° C. and hybridized with the capture probe and then electrophoresis is performed, a 2500 bp DNA band which looks larger about 8 times than a 320 bp PCR product can be seen. In an electrophoresis, since mobility of a DNA is sensitive to a three-dimensional structure of the DNA, it is difficult to assume a precise size. However, there is no doubt that the DNA positioned at about 2500 bp is a DNA complex formed between the capture probe and the asymmetric PCR product. In case of a symmetric PCR product, the amount of DNA positioned at about 2500 bp is insignificant (Lane 2 of FIG. 3(a)). Even if a genotyping primer set is used, a DNA complex positioned at about 2500 bp can be assembled (FIG. 3(b)). If each of a forward chain and a reverse chain is labeled with Cy5, the DNA positioned at about 2500 bp includes the capture probe, the forward chain, and the reverse chain (Lanes 3 and 4 of FIG. 4). A normal double-stranded DNA does not have such a structure. As depicted in FIG. 2, this structure includes a single-stranded DNA site and a gap and can be decomposed by treating a S1 nuclease (Lanes 5 and 6 of FIG. 4). Further, if an asymmetric PCR is implemented, a DNA positioned at about 600 bp is generated (FIGS. 3 and 4). Since this DNA is labeled only with a Cy5 reverse primer and decomposed by treating a S1 nuclease, this DNA is a single-chain DNA generated by the asymmetric PCR. It has been well known that mobility of a single-chain DNA is different from that of a double-chain DNA in an electrophoresis.

Number of Forward Chain and Reverse Chain Per Capture Probe within Branched DNA Complex A product obtained by implementing integrated process using an asymmetric PCR (PCR, thermal denaturation, and hybridization with a probe) and labeling only one of two PCR primers and a capture probe with Cy5 is electrophoresed and a Cy5 intensity of a branched DNA positioned at about 2500 bp is measured and compared (see FIG. 5(b)). The result shows that three reverse chains and two forward chains are bonded to each capture probe. That is, the resultant structure seems to be similar to the structure depicted in FIG. 2(c). Therefore, it is possible to draw a conclusion that if each chain is labeled, five signals per capture probe can be obtained.

Condition for Promoting Assembly of Branched DNA Complex

It is possible to self-assemble a branched DNA complex even if an asymmetric PCR is implemented with a capture probe. If hybridization is implemented after an asymmetric PCR and thermal denaturation are implemented, assembly of a branched DNA is promoted about 5 times (Lane 3 of FIG. 6(a)). If EDTA is added during the hybridization to suppress generation of DNA, the assembly of the branched DNA is remarkably suppressed (FIG. 6(b)). The results show that the assembly of the branched DNA is promoted by generating a DNA with a PCR primer, a dNTP, and a DNA polymerase existing in a PCR mixture during the hybridization. If the thermal denaturation is not implemented after the asymmetric PCR, the self-assembly cannot be promoted during the hybridization (Lane 2 of FIG. 6(a)). Therefore, in order to promote the assembly of the branched DNA complex, the thermal denaturation is required after the asymmetric PCR. This means that thermal denaturation results in single chains formed from a double-stranded PCR product and the single chains need to be bonded to a PCR primer in order to generate a new DNA during hybridization.

Evidence of Assembly of Branched DNA Complex on Solid Surface

Figure 7:
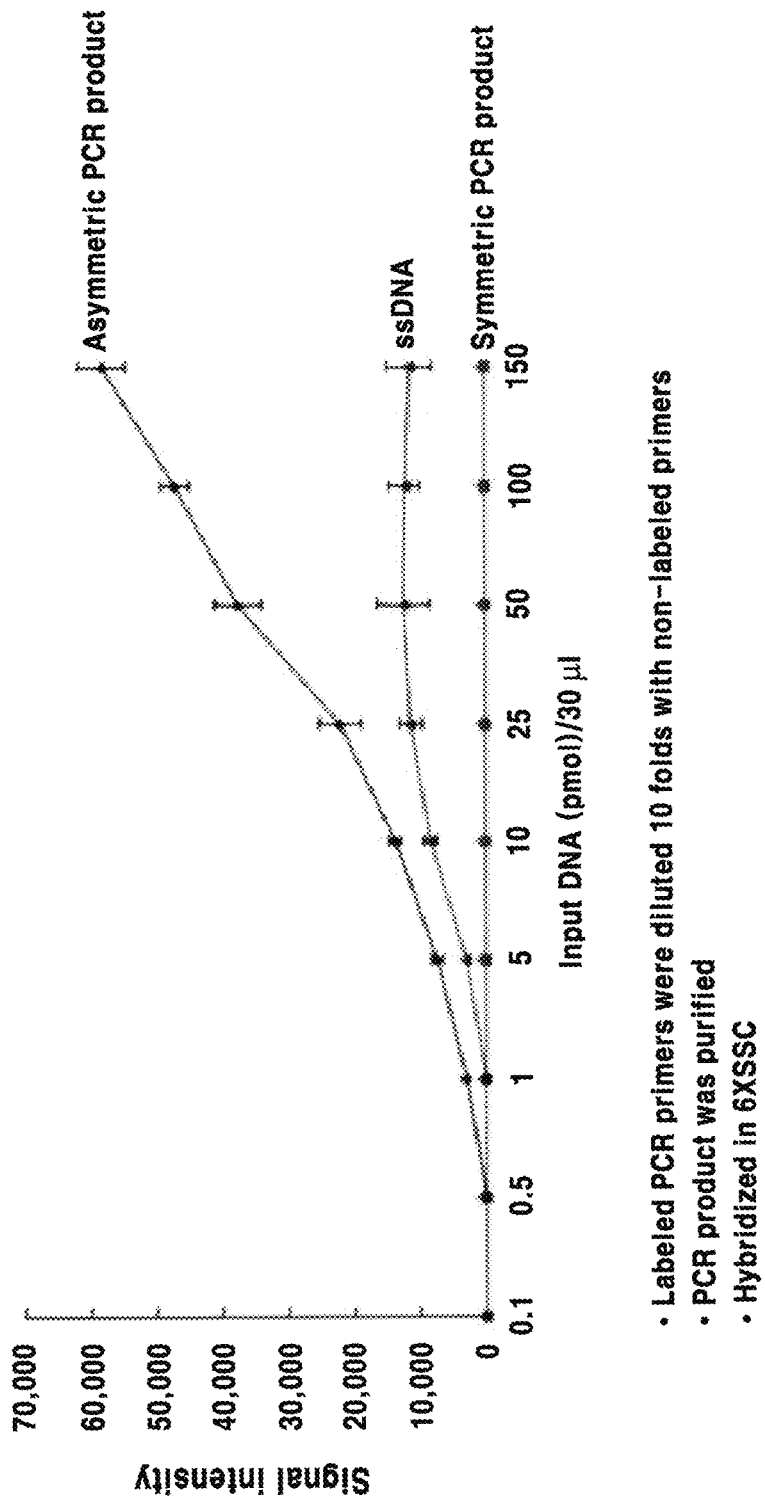
FIG. 7 is a graph showing a signal obtained from an increase in amount of a PCR product and a single-chain PCR product caused by hybridization with a HPV16 probe fixed onto a glass slide.

Additional evidence of assembly of a branched DNA can be obtained by comparing signals acquired during hybridization of a single-chain DNA, an asymmetric PCR products, a symmetric PCR product with capture nucleic acid probe fixed onto a glass slide. As depicted in FIG. 7, a signal obtained when the amount of single-chain DNA is saturated corresponds to about 10,000 unit. This means the maximum signal which can be obtained by a 100% duplex formed between the fixed capture probe and the complementary single-chain DNA (about 20 μmol/30 μl). When the greater amount of duplex DNA is added (for example, about 150 pmol), there is no detectable signal. Meanwhile, the asymmetric PCR product generates a signal greater several times than the signal obtained by the single-chain DNA. This clearly shows that the asymmetric PCR product of one or more molecules can be bonded to each fixed capture probe by formation of the branched DNA depicted in FIG. 2. In this experiment, since a signal of the asymmetric PCR product generates is too high, a fluorescence-labeled primer is diluted 10 folds with a non-fluorescence primer to compare experimental results in an appropriate range.

Importance of One Round of DNA Replication During Hybridization on Slide

Figure 8:
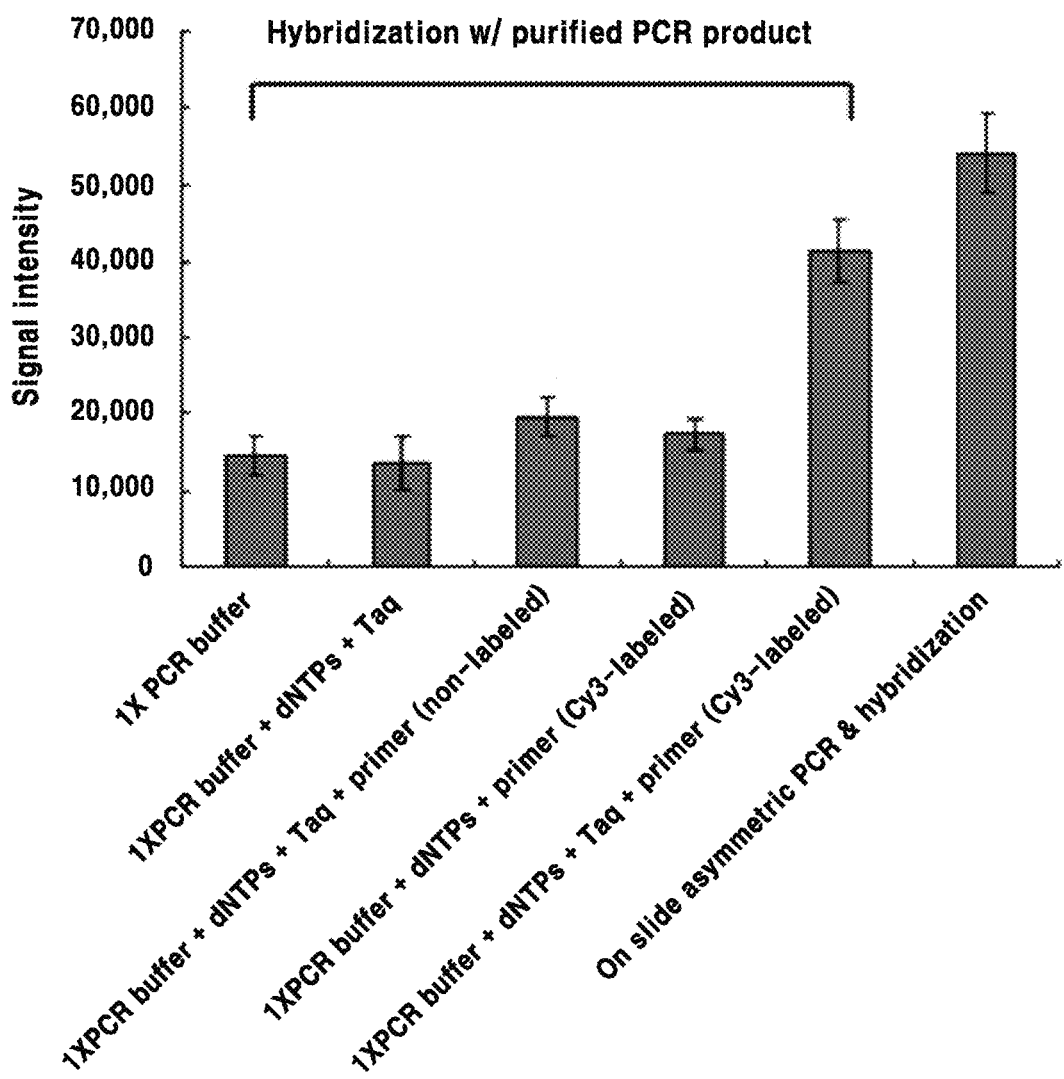
FIG. 8 is a graph proving that when an asymmetric PCR and subsequent hybridization are implemented on a surface of a DNA microarray slide, there is a severalfold increase in signal.

When a labeled asymmetric PCR product is purified and hybridized with a capture probe fixed onto a slide, under presence of a completely asymmetric PCR mixture, there is a several fold increase in signal (second bar on the right of FIG. 8). The increased signal is very similar to a signal obtained by integrated implementation of an asymmetric PCR, thermal denaturation, and hybridization on a surface of the fixed capture probe (first bar on the right of FIG. 8). This suggests that one round of DNA replication during hybridization (typically, at about 50° C. to about 60° C.) is important to an increase in signal. Another example proving this is as follows. An increase in signal during hybridization depends on a labeled PCR primer added during the hybridization (compare a third bar with a fifth bar on the left of FIG. 8). This result shows that a dramatic increase in signal can be obtained by implementing an asymmetric PCR in a tube, delivering the whole inclusion to a chamber on a microarray slide, and implementing hybridization after a thermal treatment or by implementing an asymmetric PCR and hybridization in an integrated manner on a surface of DNA microarray.

Figure 9:
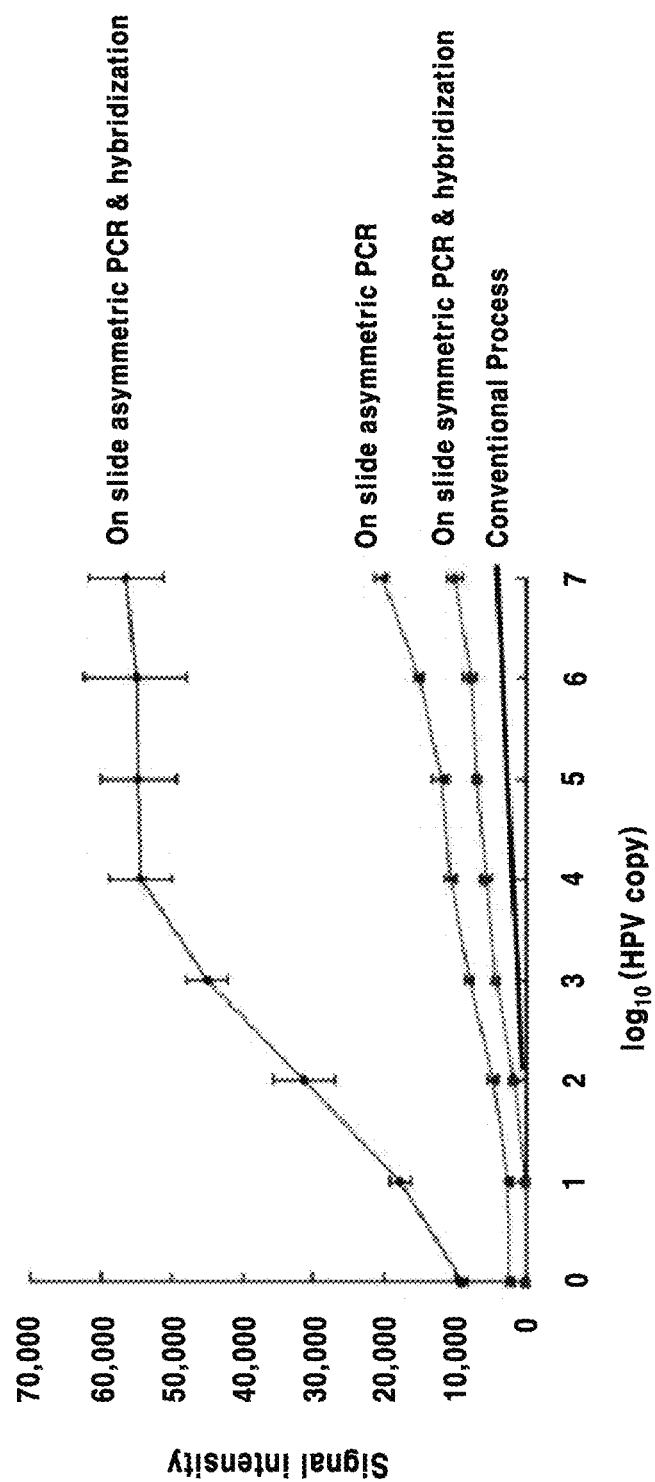
FIG. 9 is a graph proving that a target DNA of a single molecule applied to a DNA microarray slide is detected with a high signal by means of integrated implementation of an asymmetric PCR, thermal denaturation, and hybridization (-•-) on a surface of the DNA microarray slide.

High Sensitivity of Integrated Asymmetric PCR and Hybridization on Microarray Slide As described above, it has been known that detection sensitivity of a target DNA by using a DNA microarray is several orders of magnitude lower than sensitivity of a real-time PCR. In order to measure sensitivity of integrated asymmetric PCR and hybridization on a microarray slide, a serially diluted HPV16 DNA is added to an asymmetric PCR mixture and a PCR, thermal denaturation, and hybridization are implemented in an integrated manner on a surface of a HPV16 capture probe. As depicted in FIG. 9, a HPV16 DNA of a single molecule is detected with a high signal and there is a linear and proportional relationship in a range of about 1 molecule to about 10,000 molecules of a HPV16 DNA. As depicted in FIG. 9, in order to appropriately compare this DNA with labeled DNAs prepared in various ways, a labeled PCR primer is diluted five folds with non-labeled primer. Actually, an obtained signal exceeds an upper detection limit of a laser scanner. There is no precedent for detection of a single target DNA molecule with high reliability (high signal) by using a DNA microarray, and the sensitivity is equal to or much greater than a performance of the newest quantitative PCR.

Figure 10:
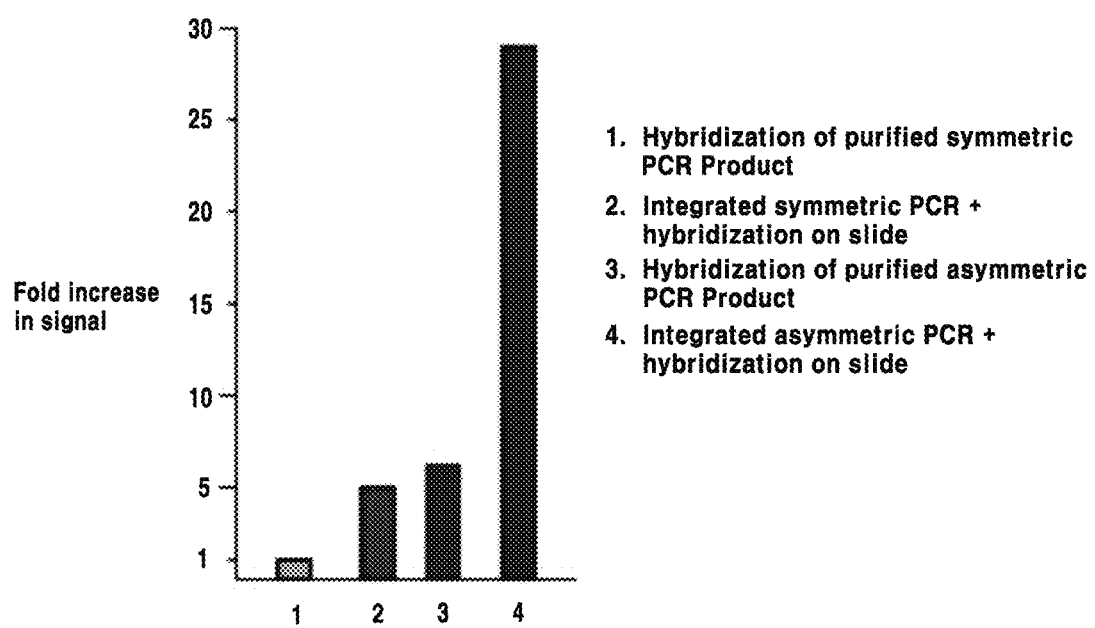
FIG. 10 is a graph in which signals obtained after various processes are compared.

A signal obtained from integrated implementation of an asymmetric PCR and hybridization is higher at least about times to about 30 times than a typical protocol recommended by a commercial DNA chip diagnostic kit (FIG. 10). In a typical process, it is recommended that a purified PCR product is hybridized in a buffer solution (for example, 3×SSC or 6×SSC) on a microarray slide. A signal (column 4) obtained by means of integrated implementation of an asymmetric PCR, thermal denaturation, and hybridization on a DNA microarray surface is greater about 30 times than a signal (column 1) obtained from the typical process, i.e. a purified symmetric PCR product and greater about 5 times than a signal (column 2) obtained by means of integrated implementation of a symmetric PCR and hybridization or a signal (column 3) obtained by means of hybridization of a purified asymmetric PCR product.

High sensitivity of the integrated implementation can be applied variously for detecting and identifying infectious agents such as viruses and microorganisms and for determining whether or not there are infectious agents in a body. Further, such an integrated implementation can be used for detecting cancer cells from many ordinary cells.

Detection of RNA with High Sensitivity by Means of Integrated Implementation

Figure 12:
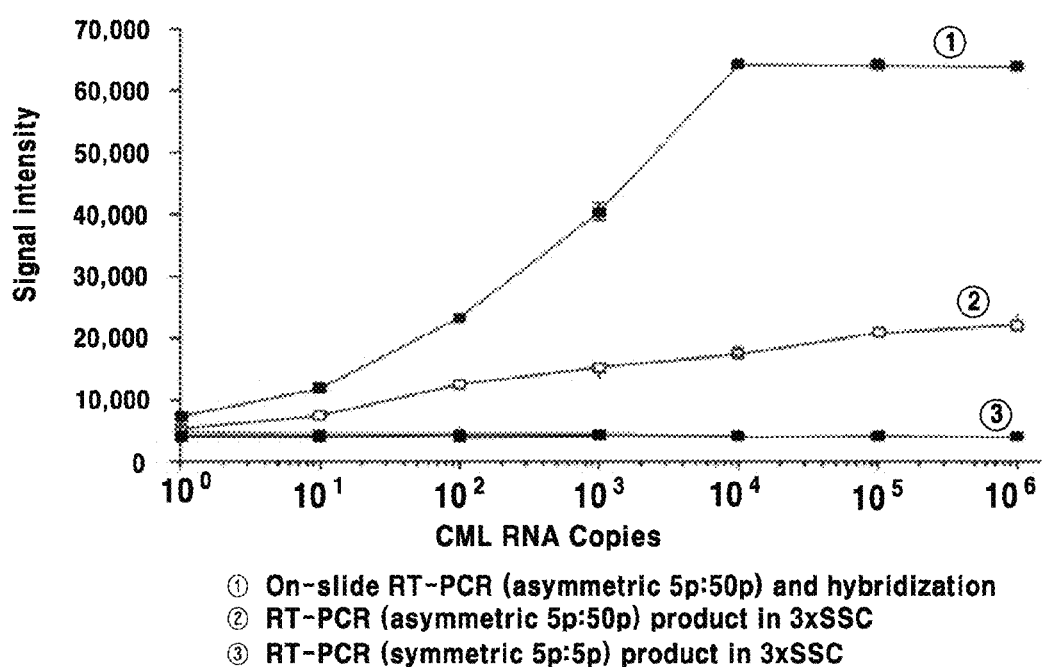
FIG. 12 is a graph proving that a RNA detection signal and sensitivity are dramatically increased by means of integrated implementation of reverse transcription, an asymmetric PCR, thermal denaturation, and hybridization on a surface of a DNA microarray slide (①): integrated implementation of reverse transcription, an asymmetric PCR, thermal denaturation, and hybridization on a slide surface; ②: hybridization of reverse transcription/asymmetric PCR product with a probe fixed in 3×SSC; and ③: hybridization of reverse transcription/symmetric PCR product with a probe fixed in 3×SSC).

Various infectious agents including a virus containing a RNA genome and a diagnosis thereof are relevant to detection of RNA. Sometimes, whether or not there is an infectious virus is determined by a quantitative PCR after purification and enrichment of a RNA sample. It has been found that integrated implementation from a RNA to hybridization can be carried out on a microarray surface. By adding an asymmetric PCR to the integrated implementation, it is possible to greatly increase a detection signal and sensitivity. As depicted in FIG. 12, a RNA of 1 molecule to 10 molecules can be easily detected by means of integrated implementation of reverse transcription, an asymmetric PCR, and hybridization on a DNA microarray surface (line ① of FIG. 12). As compared with a case where there are 10,000 subject RNAs added as shown in FIG. 12, a signal obtained by means of an asymmetric PCR and hybridization is greater about 5 times than a signal obtained by means of an asymmetric PCR only (line ② of FIG. 12).

Figure 13:
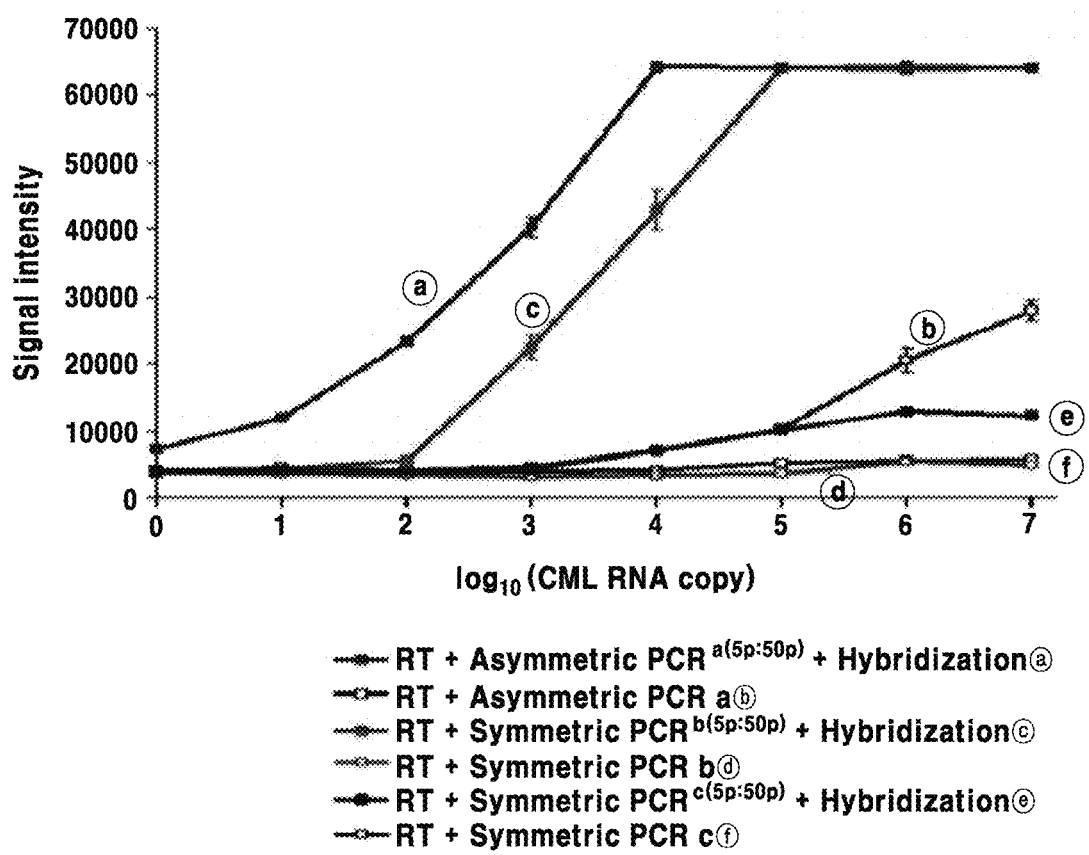
FIG. 13 is a graph showing that there is a great increase in signal when a concentration of a primer is increased during a symmetric PCR.

Further, as shown in lines ⓒ and ⓓ of FIG. 13, there is a great increase in signal by means of integrated implementation of a symmetric PCR and hybridization with a tenfold increase in both a forward primer and a reverse primer. However, the increased sensitivity cannot reach sensitivity obtained by means of an asymmetric PCR (compare a line ⓐ with a line ⓒ in FIG. 13).

Combination of Integrated Implementation and Simple Nucleic Acid Extract Process Typically, a nucleic acid is separated from a specimen to be studied or diagnosed and purified, and the purified nucleic acid is used to amplify and hybridize a target gene. However, depending on a specimen and a purpose of diagnosis, a specimen (particularly, blood, serum, a cell, and the like) can be processed simply and a diagnosis target gene can be amplified. Accordingly, such a process can be used to automate a gene diagnosis.

Figure 14:
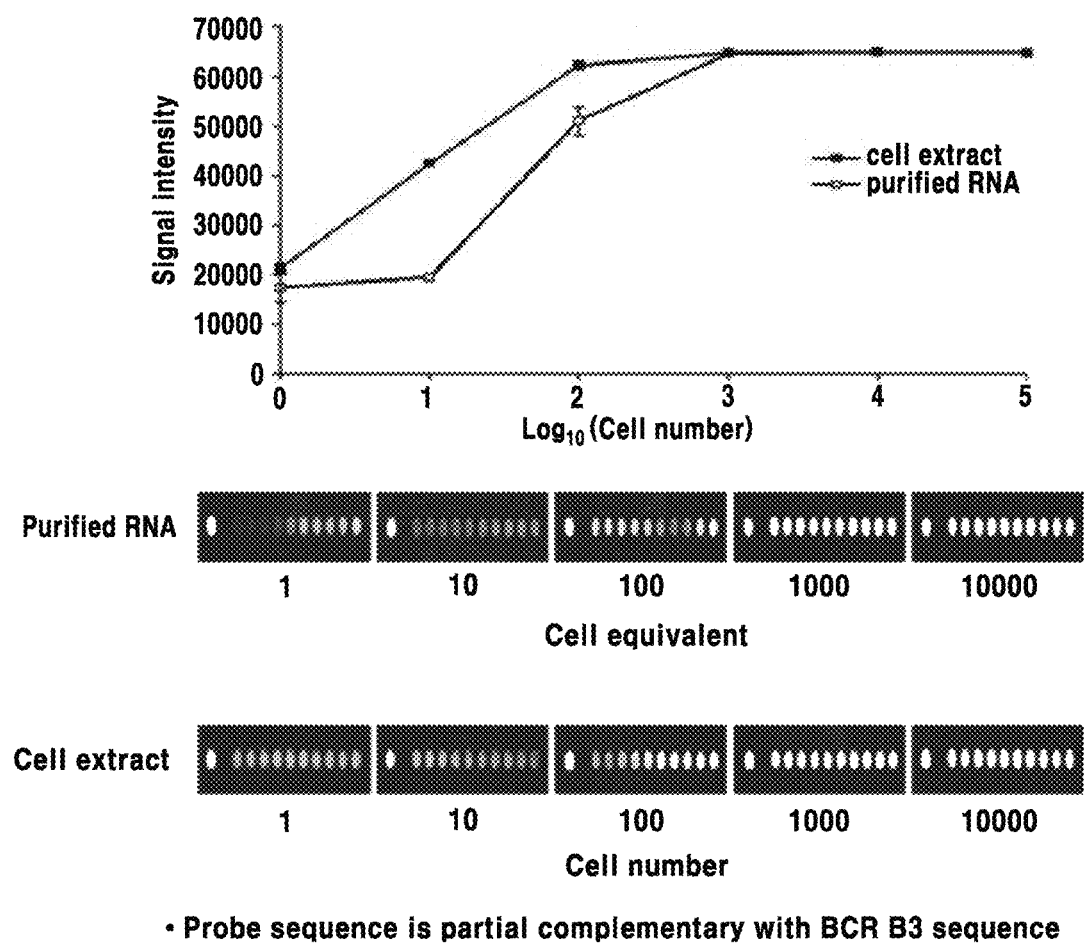
FIG. 14 shows detection of a chimeric BCR-ABL RNA by directly adding a heated chronic myeloid leukemia cell-extract to integrated implementation of reverse transcription, an asymmetric PCR, and hybridization on a microarray slide.

As depicted in FIG. 14, if a chronic myeloid leukemia cell is thermal-treated, a nucleic acid released can be used in association with integrated implementation, i.e. direct reverse transcription, a PCR, and hybridization. A signal and sensitivity is similar to those of a purified RNA. Accordingly, such a process can be used to simplify and automate a gene diagnosis.

Opinion on Assembly of Branched DNA by Using Asymmetric PCR Product

A symmetric PCR product has a very low speed or efficiency of being bonded to a capture probe as compared with an asymmetric PCR product or a single chain. This is because a speed or efficiency of renaturation (a returning process of double chains to a duplex) of the symmetric PCR product after denaturation is higher than the speed or efficiency of being bonded to a capture probe. In particular, a speed of being hybridized with a capture probe fixed on a solid surface is lower. Meanwhile, since the single-chain DNA has a high probability of collision with a capture probe, a speed or efficiency of hybridization is high. This has been proved experimentally. In case of an asymmetric PCR, a single-chain DNA is additionally generated, and, thus, the single chain has a high speed or efficiency of being bonded to a capture probe as compared with the symmetric PCR product. There has been a report related to this. As can be seen from FIG. 2(a), in order to form a branched DNA, a single chain complementary to a capture probe needs to be bonded first. Therefore, the asymmetric PCR product is more useful for forming a branched DNA than the symmetric PCR product. The reason why assembly of the branched DNA is promoted during hybridization in a PCR mixture is one round of DNA generation. Other detailed mechanisms for explaining the reason have not been provided.

MODE FOR CARRYING OUT THE INVENTION

Example 1

Condition for PCR and Hybridization for Detecting HPV DNA

A capture probe and a PCR primer used for detecting a HPV16 DNA are shown in FIG. 1 and a detailed sequence thereof is as follows.

PCR Primer Set A:
Primer having sequence entirely complementary to a HPV16 L1 site

```
                            (sequence No. 1)
Forward primer (F):    5'-GATGGTAGTATGGTTCATACTGGCTTTGG-3'

(sequence No. 2)
Reverse primer (R):    5'-GCATCAGAGGTAACCATAGAACCACTAGG-3'
```

PCR Primer Set B:
Common primers used for genotyping of about 40 kinds of HPVs were prepared to recognize HPV L1 sites of the all HPVs each having a slight difference in sequence.

```
                            (sequence No. 3)
Forward primer (GP4F): 5'-GATGGTGATATGGTAGATACAGGATTTGG-3'

(sequence No. 4)
Reverse primer (GP4R): 5'-GCGTCAGAGGTTACCATAGAGCCACTAGG-3'
```

Capture Probe:

```
                            (sequence No. 5)
HPV16 capture probe:   5'-CTCTGGGTCTACTGCAAATTTAGCCAGTT-3'

(sequence No. 6)
HPV18 capture probe:   5'-CACAGGTATGCCTGCTTCACCTG-3'
```

In a PCR primer, a 5' end was labeled by connecting it with one of Cy3 and Cy5. A capture probe typically has a terminal amine group at a 5' end and a carbon linker therebetween.

The primer and the capture probe were derived from a HPV L1 site (as described in GenBank accession number K02718 and Korean Patent Laid-open Publication No. 10-2006-0019042). Specificity of capture probes used in the present disclosure was already proved (Korean Patent Laid-open Publication No. 10-2006-0019042; Kim K T, Na C H, Yun Y M, Hwang T S, Kim S N, Chae C B Analytical Biochemistry 2010 396:139-145)

Preparation of Symmetric PCR Mixture:
A PCR mixture (30 μl) contained the following materials: 30 mM of Tris-HCl (pH 9.3), 30 mM of KCl, 30 mM of NH$_4$Cl, 2 mM of MgCl$_2$, 0.4 mM of each of dNTP, 0.4 mM of Taq DNA polymerase, 5 pmol of Cy3-labeled forward primer, 5 pmol of Cy3-labeled reverse primer, and a DNA template.

Preparation of Asymmetric PCR Mixture:
A PCR mixture was the same as the above-described symmetric PCR mixture except the following materials: 5 pmol of Cy3-labeled forward primer and 50 pmol of Cy3-labeled reverse primer.

PCR Cycle:
A PCR was implemented as follows: a heat treatment at about 94° C. for about 5 minutes; 30 cycles of a heat treatment at about 94° C. for about 1 minute, at about 50° C. for about 1 minute and at about 72° C. for about 1 minute; and a final heat treatment at about 72° C. for about 5 minutes.

Purification of PCR Product:
According to a protocol provided by Qiagen, a PCR product was bonded to a glass membrane and purified from a free primer.

Separation of Two Chains of PCR Product:
In order to separate two chains of a PCR product, in one of primers, a 5' end was labeled with biotin and in the other primer, a 5' end was labeled with Cy3. After a PCR, the PCR product was purified as described above. The purified product was bonded to streptavidin bonded to a magnetic bead and heated at about 95° C., so that a Cy3-labeled chain was released. The released chain was collected and quantitated.

Example 2

Formation of Branched DNA Complex (Aggregated DNA) Between Asymmetric PCR Product and Capture Probe In order to prove that a DNA complex greater than the PCR product was formed in case of hybridization of a capture probe with a PCR product, a HPV16 plasmid was amplified by means of a symmetric PCR and an asymmetric PCR and heat-treated at about 95° C. for about 5 minutes and then hybridized with a HPV16 capture prove at about 50° C. for about an hour. Then, a DNA was analyzed by polyacrylamide gel electrophoresis and the result thereof is provided in FIG. 3.

FIG. 3 is an electrophoresis result image proving assembly of aggutinates (or a branched DNA) between a capture probe and an asymmetric PCR product. FIG. 3(a) shows that a symmetric PCR and an asymmetric PCR were implemented with a primer set A having a sequence entirely complementary to a HPV16 L1 site, a 29 nt HPV16 capture probe was added to the reaction mixture, a DNA was denatured at about 95° C., and hybridization was implemented at about 50° C. This process was performed in a single PCR mixture. The DNA was separated by polyacrylamide electrophoresis and stained with EtBr (ethidium bromide). In the symmetric PCR, a ratio of a F primer to a R primer was about 1:1, and in the asymmetric PCR, a ratio of a F primer to a R primer was about 10:1. Lane 1—symmetric PCR+hybridization; Lane 2—symmetric PCR+capture probe+hybridization; Lane 3: asymmetric PCR+hybridization; and Lane 4: asymmetric PCR+capture probe+hybridization. DNAs positioned at about 600 bp in Lanes 3 and 4 were single-strand DNA (320 nucleotide) generated by means of an asymmetric PCR and mobility thereof was lower than that of a double-chain PCR product (320 bp) in an electrophoresis. A DNA positioned at about 2500 bp in Lane 4 was a branched DNA complex. Mobility of the branched DNA was also lower than the double-chain DNA. FIG. 3(b) shows a result of an experiment with a genotyping primer set B. Explanation of Lanes is the same as provided in FIG. 3(a). In case of a symmetric PCR with a genotyping primer, a non-specific DNA was generated but a branched DNA was not assembled under presence of a capture probe.

As can be seen from FIG. 3(a), an asymmetric PCR product generated by using the PCR primer set A formed a DNA complex positioned at about 2500 bp and greater than a capture probe and a PCR product (320 bp). Meanwhile, in case of a symmetric PCR under presence of a capture probe, the amount of DNA complex positioned at about 2500 bp was insignificant. In case of a DNA amplified by using the genotyping primer set B (FIG. 3(a)), an asymmetric PCR product formed a DNA complex positioned at about 2500 bp with a capture probe and a symmetric PCR product did not assemble a complex with a capture probe. In an electrophoresis, mobility of the DNA was sensitively affected by a three-dimensional structure of the DNA, it is difficult to assume a precise size or structure. In case of the symmetric PCR with the genotyping PCR primer, a non-specific product (positioned at about 600 bp) was seen. However, they were not involved in formation of a DNA complex as can be seen from FIG. 3(b).

Example 3

In order to get information of a structure of a complex, an asymmetric PCR was implemented with a genotyping primer Cy5-GP4F or Cy5-GP4R, denaturation was implemented at about 95° C., hybridization with a capture probe was implemented, and a DNA was purified. The purified DNA was treated with S1 nuclease specific to a single-strand and electrophoresed. Then, a Cy5 image was scanned with a LAS 4000 image analyzer and the result thereof is provided in FIG. 4.

FIG. 4 shows that a branched DNA complex includes not a normal double-chain DNA but a single-chain site and a gap. In case of an asymmetric PCR with a genotyping primer set B, a PCR was implemented with a Cy5-labeled forward primer or a Cy5-labeled reverse primer, a capture probe was added, denaturation was implemented at about 95° C., and hybridization was implemented at about 50° C. After a DNA was purified, it was treated with S1 nuclease specific to a single-chain and electrophoresed. FIG. 4(a) is an image of EtBr staining. FIG. 4(b) is a Cy5 image. Asymmetric PCR+hybridization: Lane 1—Cy5-GP4F primer; Lane 2—Cy5-GP4R primer asymmetric PCR+capture probe+hybridization; Lane 3—Cy5-GP4F primer; and Lane 4—Cy5-GP4R primer. In case of DNAs of Lanes 3 and 4 processed with S1 nuclease: Lane 5—Cy5-GP4F primer; and Lane 6—Cy5-GP4R primer.

It was found that a branched DNA positioned at about 2500 bp contained a capture probe, a forward chain, and a reverse chain. Since the branched DNA could be decomposed with a S1 nuclease (FIG. 4), it might have a single-chain site and a gap as shown in FIG. 2. In case of an asymmetric PCR, a reverse strand was generated by using a Cy5-GP4R primer at a position of about 600 bp but in case of using the Cy5-GP4F primer, there was no DNA at the same position (FIG. 4(b)). Therefore, a DNA positioned at about 600 bp was a reverse single-chain DNA generated by means of an asymmetric PCR. Such a DNA could be decomposed with a S1 nuclease (FIG. 4). It was well known that mobility of a single-chain DNA is different from that of a duplex DNA in an electrophoresis.

Example 4

Number of Reverse Chain and Forward Chain Per Capture Probe within Branched DNA Complex When integrated implementation (asymmetric PCR, denaturation, and hybridization) was carried out with a capture probe, one of two genotyping PCR primers and a capture probe was labeled with Cy5. After electrophoresis, a Cy5 image was analyzed with a LAS 4000 image analyzer and the result thereof is provided in FIG. 5.

Figure 5:
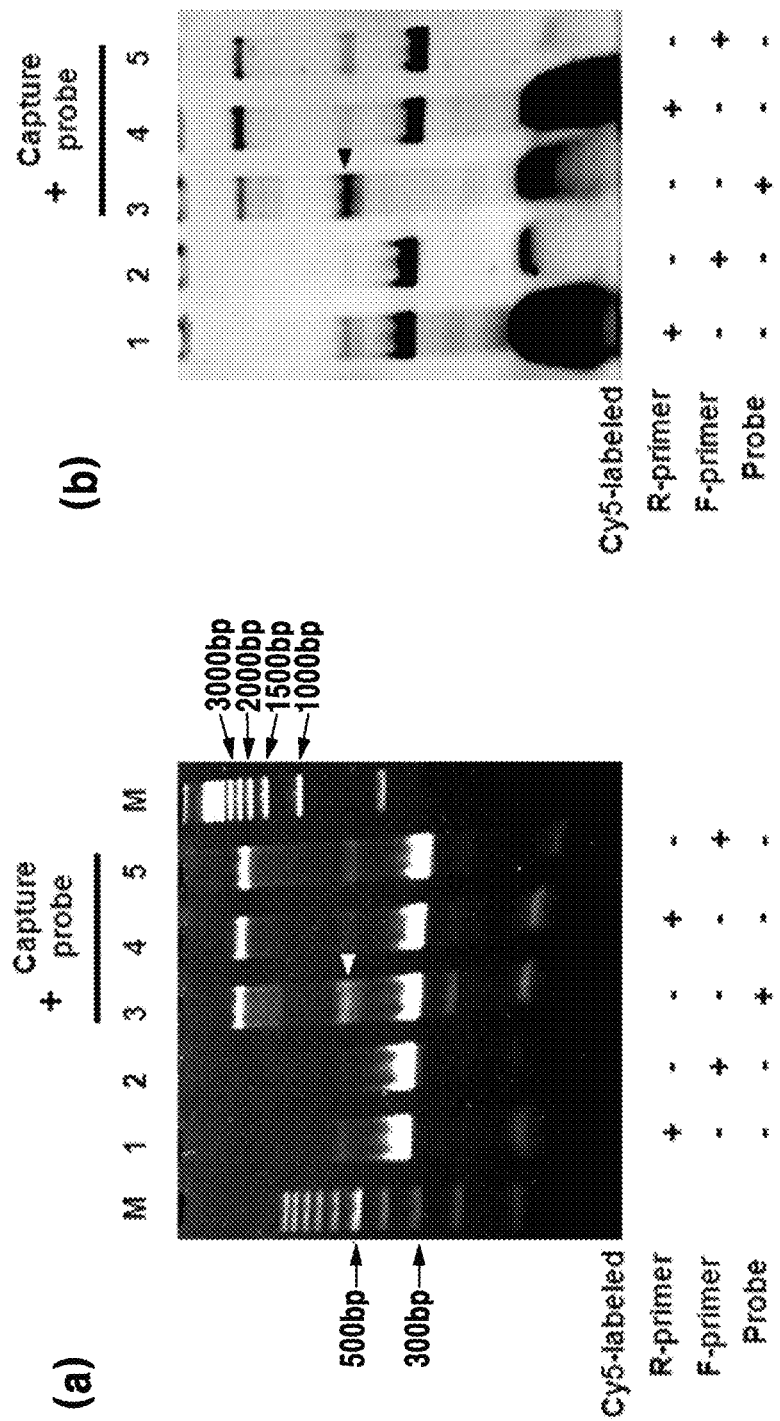
FIG. 5 is an electrophoresis result image showing a result of an experiment of determining the number of forward and reverse chains bonded to each capture probe existing in a branched DNA.

FIG. 5 shows a result of an experiment of determining the number of forward and reverse chains bonded to each capture probe existing in a branched DNA. With genotyping primers and HPV16 capture probe, an asymmetric PCR was implemented, denaturation was implemented at about 95° C., and hybridization was implemented at about 50° C. The process was performed by using two primers and a capture probe one of which was labeled with Cy5. After electrophoresis and scanning with a LAS 4000 imager, intensities of a branched DNA positioned at about 2500 bp was compared. FIG. 5(a) is an image of EtBr staining. FIG. 5(b) is a Cy5 image. In case of integrated implementation without a capture probe: Lane 1—Cy5-GP4R; and Lane 2—Cy5-GP4F. In case of integrated implementation with a capture probe: Lane 3—Cy5-capture probe; Lane 4—Cy5-GP4R; and Lane 5—Cy5-GP4F.

Signal intensities of three DNAs, i.e. a capture probe, a reverse chain, and a forward chain, in a branched DNA complex positioned at about 2500 bp were compared with each other. As a result, it was found that each probe contained three reverse chains and two forward chains.

Example 5

Hybridized Pattern of Single-Chain DNA, Symmetric PCR Product, and Asymmetric PCR Product By using a genotyping primer, ssDNA, a symmetric PCR product, and an asymmetric PCR product in various amounts were dissolved in 30 μl 6×SSC and heated at about 94° C. for about 5 minutes and immediately cooled in ice water. The heated mixture was added to a chamber bonded to an upper part of a microarray to which a HPV16 capture probe was fixed and incubated (hybridized) at about 50° C. for about an hour. After the incubation, the chamber was pilled off and a glass slide was immersed in each of the following solutions for about 5 minutes: ×SSC-0.1% SDS, 0.1×SSC-0.1% SDS, and 1×SSC. Finally, the slide was rinsed with deionized water and dried.

The dried glass slide was scanned with a laser scanner (Scan Array Express, Perkin Elmer, Co) and its fluorescent image was scanned to quantitate an intensity of a fluorescent spot.

In this experiment, to appropriately compare the resultant product with a product obtained by another DNA generating method, a PCR was implemented under presence of a Cy3-labeled primer diluted tenfold with a non-labeled primer, and the result thereof is provided in FIG. 7.

FIG. 7 is a graph showing a signal obtained from an increase in amount of a PCR product and a single-chain PCR product caused by hybridization with a HPV16 probe fixed onto a glass slide. A single-chain DNA (ssDNA) (-▲-) was extended by a Cy3-labeled reverse primer and purified from a PCR product. The signal was obtained depending on the amount of the ssDNA that saturated the fixed capture probe (i.e. the amount corresponding to the amount of a 100% duplex DNA formed and the fixed capture probe). A signal obtained by using an asymmetric PCR product (-●-) significantly exceeded a saturated signal obtained by using the ssDNA. To appropriately compare with results obtained by using another DNA, a Cy3-labeled primer was diluted tenfold with a non-labeled primer. A symmetric PCR product (-■-) hardly showed an increase in signal under the present experimental conditions.

As depicted in FIG. 7, a fixed HPV16 oligonucleotide was saturated with the ssDNA at about 25 pmol and a signal of about 10,000 unit was obtained. This value was corresponded to the value obtained by the 100% duplex formed between the HPV16 capture probe and the ssDNA. The symmetric PCR product did not form a significant level of duplex at about 150 pmol. Meanwhile, the asymmetric PCR product generated a signal in multiple higher than a signal obtained by using a saturation amount of the ssDNA. This means that an asymmetric PCR product of one or more molecules is bonded to a single molecule of a fixed HPV16 oligonucleotide probe. The reason why formation of a duplex with a fixed probe by using a symmetric PCR product was insignificant was that self-assembly of a duplex between two complementary chains of the symmetric PCR product was overwhelming but an interaction between the duplex and the fixed oligonucleotide was insignificant.

Example 6

Promotion of Assembly of Branched DNA by Generating DNA During Hybridization in Solution When an asymmetric PCR was implemented under presence of a HPV16 capture probe in the same manner as Example 1, denaturation was implemented at about 95° C. and then hybridization was implemented at about 50° C. for about an hour, a branched DNA was assembled (FIG. 6(a)). Meanwhile, when only an asymmetric PCR was implemented or when hybridization was implemented after an asymmetric PCR without denaturation, assembly of a branched DNA was insignificant (FIG. 6(a)). The result shows that the assembly of the branched DNA was promoted during the hybridization after the denaturation. It also shows that since all elements required for generating a DNA existed during the hybridization, one-round DNA synthesis was important. In case of adding EDTA during the hybridization, DNA synthesis was stopped. In that case, the assembly of the branched DNA was remarkably suppressed (FIG. 6(b)). When an asymmetric PCR was implemented with a primer set A or a primer set B, the same result was obtained.

Figure 6:
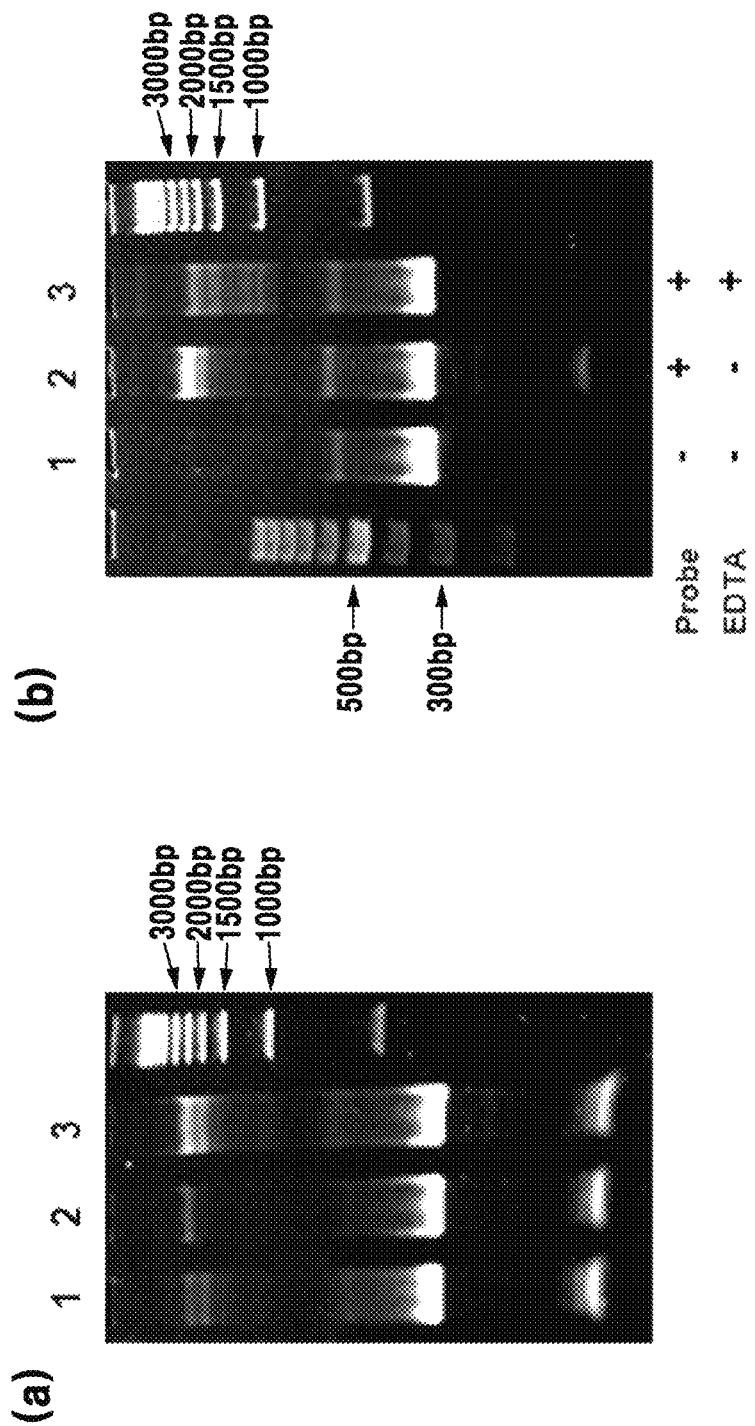
FIG. 6 shows a result of an experiment under conditions for branched DNA formation.

FIG. 6 shows a result of an experiment under conditions for branched DNA formation. FIG. 6(a) shows a state where an asymmetric PCR was implemented with a capture probe and stopped (Lane 1), a state where hybridization was implemented without denaturation after an asymmetric PCR (Lane 2), and a state where denaturation was implemented at about 95° C. after an asymmetric PCR and hybridization is implemented at about 50° C. (Lane 3). FIG. 6(b) shows a state where an asymmetric PCR was implemented and denaturation and hybridization were implemented without a capture probe (Lane 1), a state where after an asymmetric PCR and thermal denaturation were implemented, a capture probe is added and hybridization is implemented (Lane 2), and a state where after an PCR and thermal denaturation were implemented, a capture probe and EDTA were added and hybridization was implemented (Lane 3). All the experiments were carried out in a PCR mixture.

Example 7

Promotion of Assembly of Branched DNA by Generating DNA During Hybridization on DNA Chip Surface By using a labeled primer which was the same as used in Example 1 except that it was diluted fivefold with a non-labeled primer, an asymmetric PCR (30 µl) was implemented with a HPV16 plasmid of about $10^5$ copies (FIG. 8). In order to produce in large amounts, the asymmetric PCR was implemented in multiple tubes. After the PCR, a product was bonded to a glass membrane and purified. The purified PCR product was incubated in various buffers as follows: a 1×PCR buffer and a 1×PCR buffer additionally including the following materials (individually or in combination, see FIG. 8): 4 dNTPs, a Taq polymerase, a non-labeled primer, and a labeled-primer (diluted fivefold with a non-labeled primer). The mixture was delivered to a chamber bonded to a surface of a microarray (to which HPV16 and HPV18 capture probes were fixed). A slide was denatured at about 95° C. for about 5 minutes and incubated at about 50° C. for about an hour. After being washed, the slide was scanned for a fluorescent image and quantitation. As depicted in FIG. 8, in case of implementing hybridization in a solution containing all elements required for the PCR, there was a great increase in signal. This signal was similar to a signal obtained when an asymmetric PCR, thermal denaturation, and hybridization were implemented in an integrated manner in a single PCR mixture on a DNA chip (FIG. 8). The result shows that assembly of a branched DNA was promoted by generating a DNA during the hybridization.

FIG. 8 is a graph proving that when an asymmetric PCR and subsequent hybridization are implemented on a surface of a DNA microarray slide, there is a several fold increase in signal. Herein, a Cy3-labeled asymmetric PCR product was purified and hybridized under various conditions. The result thereof was compared with a result (first column on the right) of integrated implementation of an asymmetric PCR and subsequent hybridization in a single PCR mixture on a DNA microarray slide surface. A result of the comparison shows that DNA replication (second column on the right) occurring during the hybridization was important for an increase in signal.

Example 8

Detection Sensitivity of Integrated Implementation of Asymmetric PCR and Hybridization A serially diluted HPV16 plasmid was amplified on a slide including fixed HPV16 and HPV18 capture probes by means of a PCR. At the end of the PCR, the slide was washed and scanned or a PCR mixture was heated at about 95° C. and incubated at about 50° C. for about an hour to continue hybridization in a single reaction mixture. In order to appropriately compare the result with results obtained from various PCR products, a Cy3-labeled PCR primer was diluted fivefold with a non-labeled primer.

As depicted in FIG. 9, when a serially diluted HPV DNA was amplified by means of an asymmetric PCR, a HPV DNA of a single molecule could be detected with a high signal. Further, there was a linear relationship between the signal and the number of HPV DNAs applied onto the slide (i.e. 1 to about 10,000 copies of the applied DNA).

Meanwhile, in another type of PCR, a signal and sensitivity were much lower as compared with the integrated implementation of the asymmetric PCR and the hybridization on the slide.

Example 9

Comparison of Signals Obtained from Various Processes

As described above, integrated implementation of a symmetric PCR and hybridization on a slide increased a signal five times as compared with hybridization of a purified PCR product on a slide. A purified asymmetric PCR product increased a signal about five times to about six times as compared with a typical process (i.e. hybridization of a purified symmetric PCR product on a slide). However, in case of implementing an asymmetric PCR and hybridization on a slide, there was an additional fivefold increase in signal (see bar 4 of FIG. 9). As a result, there was about thirtyfold increase in signal as compared with the typical process of purifying and hybridizing a symmetric PCR product (bar 1 of FIG. 9). A dramatic increase in signal (and accompanying sensitivity) was difficult to predict but it was found.

Example 10

Dramatic Increase in Signal and Sensitivity by Means of Integrated Implementation of Reverse Transcription, Asymmetric PCR, and Hybridization for RNA Detection A chronic myeloid leukemia cell line K562 was grown in a culture medium and a RNA was extracted. The chimeric BCR-ABL (type B3-A2) RNA content was measured by means of a real-time quantitative PCR. An one-step reverse transcription and PCR mixture (30 μl in total) was prepared as follows: a 12 μl premixed reaction mixture (Intron Co.) containing 4 dNTPs, a buffer, a reverse transcriptase, and a DNA polymerase; a labeled reverse (A2-R) and forward (B2-F) primers (diluted twofold with a non-labeled primer); and a RNA.

Typically, 5 pmol of Cy3-forward primer and 50 pmol Cy5-reverse primer were added for an asymmetric PCR. A labeled forward primer of 5 pmol and a labeled reverse primer of 5 pmol were added for a symmetric PCR.

Thermo-cycling was performed as follows: 45 cycles of a treatment at about 45° C. for about 30 minutes and at about 95° C. for about 5 minutes, (at about 94° C. for about 15 seconds, at about 55° C. for about 15 seconds, at about 72° C. for about 15 seconds).

Figure 11:
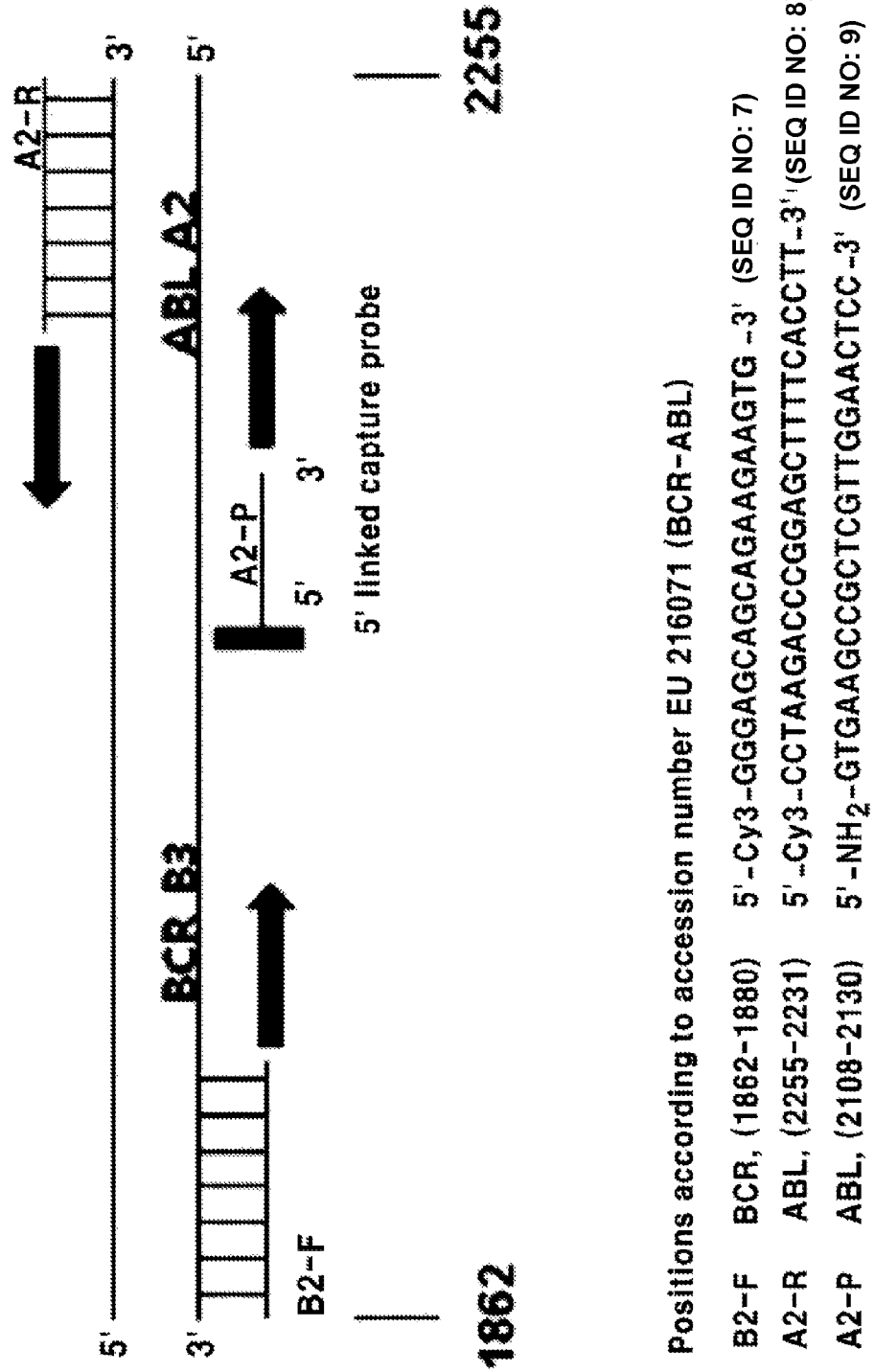
FIG. 11 schematically shows detection of a chimeric BCR B3-ABL A2 RNA from a chronic myeloid leukemia cell by means of reverse transcription, amplification, and hybridization with a capture probe (A2-P) fixed onto a glass surface.

FIG. 11 shows a capture probe and gene-specific RT-PCR primers used to detect CML fusion transcripts and sequences thereof are as follows:

```
                                              (sequence No. 7)
Forward primer (B2-F):     5'-GGGAGCAGCAGAAGAAGTG-3'

(sequence No. 8)
Reverse primer (A2-R):     5'-CCTAAGACCCGGAGCTTTTCACCTT-3'

(sequence No. 9)
ABL A2 capture probe (A2-P):  5'-GTGAAGCCGCTCGTTGGAACTCC-3'
```

A combined reaction mixture was delivered to a chamber bonded to an upper surface of a DNA microarray for integrated implementation of reverse transcription, a PCR, and hybridization. A glass slide was positioned on a heating block of a PCR device (Thermo, USA). Thermo-cycling was performed as described above. At the end of the PCR cycle, the glass slide was heated at about 95° C. for about 5 minutes and incubated (hybridized) at about 55° C. for a certain time period.

FIG. 12 shows that there was a dramatic increase in signal and sensitivity by means of integrated implementation of reverse transcription, an asymmetric PCR, and hybridization as compared with a typical process (compare a line 1 with a line 3 in FIG. 12) in the same manner as a case of detecting a DNA. A RNA of 1 molecule to 10 molecules was detected with high reliability (high signal). There was an increase in sensitivity of from about 100 times to about 1000 times as compared with a typical process (i.e. a RT-PCR in a tube and hybridization on a microarray slide; line 3 of FIG. 12).

In the same manner as a case of detecting a DNA, there was a great increase in signal and sensitivity by means of integrated implementation of reverse transcription, an asymmetric PCR, and hybridization as compared with implementation of a RT-PCR only on a slide (compare a line ⓐ and a line ⓑ in FIG. 13). During a symmetric PCR with forward and reverse primers each having a higher concentration in integrated implementation, there might be a great increase in signal by means of promotion of branched DNA formation (see lines ⓒ and ⓓ in FIG. 13). However, detection sensitivity was not as high as sensitivity shown in the integrated process including the asymmetric PCR (compare a line ⓐ with a line ⓐ in FIG. 13).

Example 11

Detection of Chimeric BCR-ABL RNA by Directly Adding Heated Cell Extract to Integrated Implementation System of Reverse Transcription, Asymmetric PCR, and Hybridization on Microarray Slide A serially diluted chronic myeloid leukemia cell line (K562) was pelleted and suspended in 50 μl Chelex-resin (BioRad). After heating at about 95° C. for about 5 minutes and centrifugation, a supernatant liquid of 5 μl was added to the reaction mixture described in Example 7. The whole mixture was delivered to a chamber bonded to an upper part of a microarray slide, and as described in Example 7, reverse transcription, an asymmetric PCR, and hybridization were implemented in an integrated manner. The slide was washed and scanned with a laser scanner. The result thereof is provided in FIG. 14. Both of a cell extract and a purified RNA showed a detection signal and sensitivity similar to those of a chimeric BCR-ABL RNA. This means that even if a RNA was not separated and purified from a cell, a diagnosis result similar to that of a purified RNA can be obtained by performing a simple heat treatment onto the cell.

The present disclosure has been explained in detail with reference to the example as above, but the present disclosure can be modified and changed in various ways by those skilled in the art within the scope of the inventive concept descried in the following claims.

INDUSTRIAL APPLICABILITY

As explained above, the present disclosure relates to a method for detecting nucleic acids by promoting formation of a branched DNA complex. In accordance with this method, a target nucleic acid detection signal and sensitivity can be dramatically increased by promoting self-assembly of a branched DNA between a single-chain oligonucleotide probe and multiple amplified target DNAs by means of integrated implementation of a PCR, thermal denaturation, and hybridization in a single reaction mixture. Therefore, this method can be used for various diagnoses and detection and can also be used to automate a diagnostic method. Accordingly, the present disclosure suggests an innovative technique for diagnosing and treating diseases.

SEQUENCE LIST FREE TEXT

An electronic file is attached.

What is claimed is:

1. A method for detecting a target nucleic acid molecule from a sample, the method comprising:
   (i) performing an asymmetric polymerase chain reaction of a single reaction mixture comprising a target nucleic acid molecule to be detected, a labeled forward primer and a labeled reverse primer in the presence of a nucleic acid probe that is attached via a linker molecule at its 5' end to a solid support, wherein the nucleic acid probe comprises a sequence entirely or partially complementary to the target nucleic acid molecule to be detected, and the labeled reverse primer is used at a concentration higher than that of the forward primer;
   (ii) thermally denaturing the amplified nucleic acid molecules in the presence of the nucleic acid probe attached to the solid support; and
   (iii) hybridizing the denatured amplified nucleic acid molecules to the nucleic acid probe at a temperature from 50° C. to 60° C., wherein the hybridization of multiple amplified nucleic acid molecules to said probe promotes formation of a branched nucleic acid complex on the solid support; and
   (iv) detecting the hybridized branched nucleic acid complex.

2. The method of claim 1, wherein the sample includes whole blood, serum, a body fluid, a body tissue, a cell, a microorganism, a virus, or a virus particle.

3. The method of claim 1, wherein before the amplification, denaturation, and hybridization are conducted, a surfactant treatment, an enzyme treatment, or a heating treatment is performed to expose a nucleic acid of the sample.

4. The method of claim 1, wherein the target nucleic acid molecule to be detected includes a mutated sequence, and the probe is complementary to the target nucleic acid molecule including the mutated sequence.

5. The method of claim 1, wherein the target nucleic acid molecule is a DNA or a cDNA which is reverse-transcribed from an RNA molecule.

6. The method of claim 1, wherein the target nucleic acid molecule is an RNA molecule, and the method further comprises reverse transcription performed before the amplification.

7. The method of claim 1, wherein the nucleic acid probe includes a single-stranded DNA or PNA sequence.

8. The method of claim 1, wherein detecting the hybridized branched nucleic acid complex includes forming a labeled complex by contacting a detectable label which is capable of binding to a double-stranded DNA with the hybridized branched nucleic acid complex.

9. The method of claim 1, wherein detecting the hybridized branched nucleic acid complex includes detecting a label in the amplified target nucleic acid molecules originating from a labeled PCR primer.

10. A method for detecting a target nucleic acid molecule in a sample, the method comprising:
(i) amplifying a target nucleic acid molecule to be detected using an asymmetric PCR using a labeled forward primer and a labeled reverse primer, wherein the labeled reverse primer is used at a concentration higher than that of the forward primer;
(ii) delivering the whole reaction mixture of (i), including the amplified target nucleic acid molecule, to a solid support surface which includes a nucleic acid probe that is attached to the solid support surface via a linker molecule at the 5' end and comprises a sequence entirely or partially complementary to the target nucleic acid molecule;
(iii) thermally denaturing the whole reaction mixture of (i) before or after the reaction mixture is delivered to the solid support surface;
(iv) hybridizing multiple amplified nucleic acid molecules denatured in (iii) with the nucleic acid probe attached to the solid support at a temperature from 50° C. to 60° C. to promote formation of a branched nucleic acid complex; and
(v) detecting the hybridized branched nucleic acid complex.

11. The method of claim 10, wherein the target nucleic acid molecule to be detected includes a mutated sequence, and the probe is complementary to the target nucleic acid molecule including the mutated sequence.

12. The method of claim 10, wherein the target nucleic acid molecule is a DNA or a cDNA which is reverse-transcribed from an RNA molecule.

13. The method of claim 10, wherein the target nucleic acid molecule is an RNA molecule, and reverse transcription is performed before the amplification.

14. The method of claim 10, wherein the nucleic acid probe includes a single-stranded DNA or PNA sequence.

15. The method of claim 10, wherein detecting the hybridized branched nucleic acid complex includes forming a labeled complex by contacting a detectable label which is capable of binding to a double-stranded DNA with the hybridized branched nucleic acid complex.

16. The method of claim 10, wherein detecting the hybridized branched nucleic acid complex comprises detecting a label inserted into the amplified target DNA by one of the labeled primers.

* * * * *